United States Patent
Miller et al.

(10) Patent No.: US 6,562,782 B1
(45) Date of Patent: May 13, 2003

(54) OLIGOCYCLOALKANOID COMPOUNDS AND METHODS OF USE

(75) Inventors: Benjamin L. Miller, Rochester, NY (US); Robert D. Hubbard, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/568,403

(22) Filed: May 10, 2000

Related U.S. Application Data
(60) Provisional application No. 60/133,361, filed on May 10, 1999.

(51) Int. Cl.[7] .................... A61K 31/015; A61K 31/198; A61K 31/405; A61K 38/02
(52) U.S. Cl. .................... 514/2; 514/414; 514/419; 514/533; 514/548; 514/563; 514/572; 514/573; 514/574; 514/601; 514/619; 514/623; 514/691; 514/715; 514/729; 530/300; 548/455; 548/496; 560/40; 560/173; 562/499; 564/82; 564/84; 564/98; 564/152; 564/153; 564/155; 564/159; 564/188; 568/367; 568/664; 568/816
(58) Field of Search .................... 435/226; 514/2, 514/414, 419, 533, 548, 563, 572, 573, 574, 601, 619, 623, 691, 715, 729; 530/300; 548/455, 496; 560/40, 173; 562/499; 564/82, 84, 98, 152, 153, 155, 159, 188; 568/367, 664, 816

(56) References Cited

U.S. PATENT DOCUMENTS

| | | | | |
|---|---|---|---|---|
| 3,325,538 A | * | 6/1967 | Foster | 562/498 |
| 6,057,362 A | | 5/2000 | Yamashita | 514/468 |

FOREIGN PATENT DOCUMENTS

| | | | |
|---|---|---|---|
| GB | 979401 | * | 1/1965 |
| JP | 62-138453 | * | 6/1988 |

OTHER PUBLICATIONS

Bell et al. Interannular Diastereoselectivity in the hybrodoration,.. J. Org. Chem. vol. 54, No. 8 pp. 1978–1987, 1989.*

Van Duzee et al. Hydrogenation and Hydrogenolysis of Ethers, J. Am, Chem.Soc. vol. 57, p. 147–151, Jan. 1935.*

Martin et al., "Cyclopropane–Derived Peptidomimetics. Design, Synthesis, Evaluation, and Structuter of Novel HIV–1 Protease Inhibitors," *J. Med. Chem.* 41:1581–1597 (1998).

Yoshida et al. "A Novel Antifungal Antiobiotic, FR–900848," *The Journal of Antibiotics* XLIII(7):748–754 (1990).

Ninomiya et al., "Chemical Study and Absolute Configuration of a New Marine Secospatane from the Brown Alga *Dilophus okamurae*," *J. Org. Chem.* 64:5436–40 (1999).

Lim et al., "An Approach to 2,3–Methanoamino Acids with Extended Side Chains: Syntheses of trans–BOC–cyclo–Lys(CBZ)–OH, trans–BOC–cyclo–Glu–OEt, and trans–BOC–cyclo–Arg(CBZ)–OH," *J. Org. Chem.* 62:9382–84 (1997).

Theberge et al., "Studies on the Diastereoselective Preparation of Bis–cyclopoanes," *J. Org. Chem.* 61:8792–98 (1996).

Taylor et al., "Oligocyclopropane Structural Units fron Cationic Intermediates," *Organic Letters* 1(8): 1257–60 (1999).

Taylor et al., "Structural Diversity Based on Cyclopropane Scaffolds," *Organic Letters* 2(5):601–603 (2000).

Yoshida et al., "A Novel Antifungal Antiobiotic, FR–900848 I. Production, Isolation, Physico–Chemical and Biological Properties," *The Journal of Antibiotics* 43(7):748–54 (1990).

Goheen G.E., "The Synthesis of Multicyclopentyls," *J. Am. Chem. Soc.* 63:744–49 (1941).

Hubbard et al., "Lewis Acid Catalyzed Diels–Alder Reactions of Highly Hindered Dienophiles," *J. Org. Chem.* 63:4143–4146 (1998).

* cited by examiner

*Primary Examiner*—Jeffrey E. Russel
(74) *Attorney, Agent, or Firm*—Nixon Peabody LLP

(57) ABSTRACT

The present invention related to an oligocycloalkanoid compound comprising formula (I)

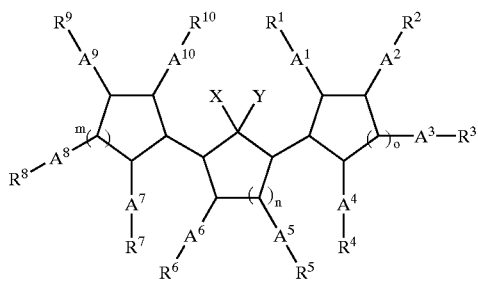

wherein m, n, and o are independently an integer from 0 to 2; $A^1$ through $A^{10}$ are independently a direct link, alkylene, alkylene-O—, carbonyl, oxygen, or sulfur; X and Y are independently hydrogen, hydroxy, alkyl, or in combination an electrophilic group; and $R^1$ through $R^{10}$ are independently hydrogen, hydroxy, alkyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoalkylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, or polypeptide, with at least one of $R^1$ through $R^4$ and at least one of $R^7$ through $R^{10}$ being other than hydrogen. Also disclosed are a pharmaceutical composition including an oligocycloalkanoid compound of the present invention, and methods of using such compounds or compositions for treating a bacterial infection, inhibiting or treating septic shock, treating a disease caused by bacterial endotoxin, and inhibiting the activity of cathepsin K.

52 Claims, 9 Drawing Sheets

OLIGOCYCLOALKANOID COMPOUNDS AND METHODS OF USE

The present application claims the benefit of U.S. Provisional Patent Application Serial No. 60/133,361, filed May 10, 1999.

FIELD OF THE INVENTION

The present invention relates to novel oligocycloalkanoid compounds, the synthesis thereof, and their methods of use.

BACKGROUND OF THE INVENTION

The design and synthesis of small, nonpeptide mimetics of polypeptide structure is a profoundly active field of research (Giannis et al., *Chem. Int. Ed. Engl.* 32:1244–1267 (1993). Peptidomimetics are of interest both from fundamental and applied perspectives (for therapeutic uses and the study of protein-protein interactions). From a practical perspective, nonpeptide compounds have several distinct advantages over their isostructural polypeptides. Firstly, polypeptides are readily recognized by peptidases and, therefore, have an extremely short lifetime in the digestive tract. Secondly, polypeptides often carry a significant number of charged moieties and, therefore, are limited in their ability to cross the blood/brain barrier. Finally, peptidomimetics are generally designed with conformational restraint in mind, allowing functional groups making up pharmacophoric moieties to be precisely positioned and gaining increased affinity for target proteins through structural rigidity.

Natural products have provided synthetic chemists with a variety of structurally novel and biologically interesting molecules. Two such natural products, which possess a repeating array of cyclopropanes, have been recently isolated. The first compound, denoted (−)-FR-900848, is a nucleoside containing natural product obtained from the fermentation broth of *Streptoverticillum fervens* HP-891, which displays potent and selective antifungal activity against *Aspergillus niger* (Yoshida et al., *J. Antiboitics* 43:748–754 (1990)). The second compound, denoted (−)-U-106305, is a potent inhibitor of cholesteryl ester transfer protein ("CETP") (Kuo et al., *J. Am. Chem. Soc.* 117:10629–10634 (1995)). Because CETP catalyzes the transformation of high-density lipoproteins to low-density lipoproteins, CETP represents an interesting target to combat atherosclerosis.

The propensity of cyclopropanes to impart rigidification into otherwise conformational mobile molecules has been used in the synthesis of constrained protease inhibitors (Lim et al., *J. Org. Chem.* 62:9382–9384 (1997)). Concurrently, methodology has been developed that uses these cyclopropanes as scaffolds for displaying functionality (Taylor et al., *Org. Lett.* 1:1257–1260 (1999); Theberge et al., *J. Org. Chem.* 61:8792–8798 (1996); and Taylor et al., *Org. Lett.* 2:601–603 (2000)). One example of the conformational bias afforded by cyclopropane moieties is the cyclopropanyl-containing molecule synthesized by Martin et al. (*J. Med. Chem.* 41:1581–1597 (1998)), which demonstrated activity as an HIV-1 protease inhibitor.

Oligocyclopropanes may serve as powerful scaffolds for the recognition of a variety of biological targets. Yet oligocycloalkanes possessing larger cyclic rings (i.e., cyclobutane, cyclopentane, cyclohexane, etc.) are virtually unmnown. Dilkamural, a naturally-occurring compound that has been identified, contains two contiguous cyclopentane ring systems (Ninomiya et al., *J. Org. Chem.* 64:5436–5440 (1999)). While a simple, non-substituted ter-cyclopentane ring system is known (Goheen, *J. Am. Chem. Soc.* 63:744–748 (1941)), no highly-substituted ter-cycloalkane ring systems are known, let alone therapeutic uses thereof.

The present invention is directed to overcoming these deficiencies in the art.

SUMMARY OF THE INVENTION

One aspect of the present invention relates to an oligocycloalkanoid compound of formula (I)

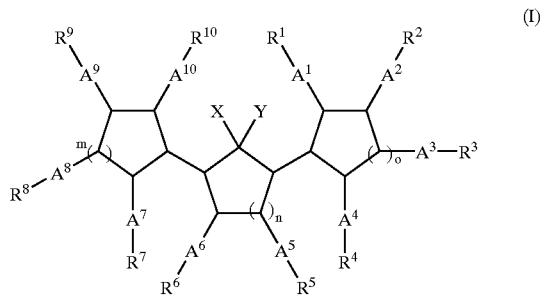

wherein m, n, and o are independently an integer from 0 to 2; $A^1$ through $A^{10}$ are independently a direct link, alkylene, alkylene-O—, carbonyl, oxygen, or sulfur; X and Y are independently hydrogen, hydroxy, alkyl, or in combination an electrophilic group; and $R^1$ through $R^{10}$ are independently hydrogen, hydroxy, alkyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoakylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, or polypeptide, with at least one of $R^1$ through $R^4$ and at least one of $R^7$ through $R^{10}$ being other than hydrogen. A pharmaceutical composition including the oligocycloalkanoid compound of formula (I) in a pharmaceutically acceptable carrier is also disclosed.

Another aspect of the present invention relates to methods of making oligocycloalkanoid compounds of the present invention, by reacting a compound selected from the group of an $R^1$ to $R^{10}$ precursor, an oxidizing agent, a reducing agent, or a deprotecting agent with a compound of formula (II) under conditions effective to prepare an oligocycloalkanoid compound of the present invention

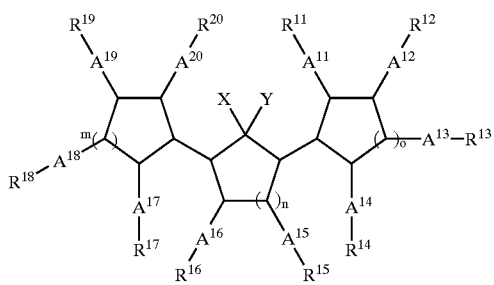

(II)

wherein m, n, and o are independently an integer from 0 to 2; $A^{11}$–$A^{20}$ are independently alkylene, alkylene-O—, carbonyl, oxygen, or sulfur; X and Y are independently hydrogen, hydroxy, alkyl, or in combination an electrophilic group; and $R^{11}$–$R^{20}$ are independenly hydrogen, hydroxy, alkyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoakylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, polypeptide, leaving group, or protecting group, with at least one of $R^{11}$ through $R^{14}$ and at least one of $R^{17}$ through $R^{20}$ being other than hydrogen.

A further aspect of the present invention relates to a method of treating a bacterial infection. This treatment method is carried out by providing an oligocycloalkanoid compound of the present invention and then administering a bacteriacidally effective amount of the oligocycloalkanoid compound to a patient having a bacterial infection, under conditions effective to treat the bacterial infection.

Another aspect of the present invention relates to a method of inhibiting or treating septic shock. This treatment method is carried out by providing an oligocycloalkanoid compound of the present invention and then administering an effective amount of the oligocycloalkanoid compound to a patient having a bacterial infection, under conditions effective to inhibit or treat septic shock resulting from the bacterial infection.

Still another aspect of the present invention relateds to a method of treating a disease caused by bacterial endotoxin. This treatment method is carried out by providing an oligocycloalkanoid compound of the present invention and then administering an effective amount of the oligocycloalkanoid compound to a patient having a bacterial infection, under conditions effective to neutralize bacterial endotoxin and thereby treat the disease caused bacterial endotoxin.

A further aspect of the present invention relates to a method of inhibiting the activity of cathepsin K. This method is carried out by providing an oligocycloalkanoid compound of the present invention and then introducing the oligocycloalkanoid compound into a system including cathepsin K under conditions effective to inhibit cathepsin K. The system can be either in vivo or in vitro.

The present invention describes an entirely new structural class of molecules, which combines synthetic simplicity with the structural complexity typically found only in natural products. Furthermore, unlike other modular structural scaffolds, these molecules are conformationally rigid, simplifying their structural analysis and prediction of target binding conformation. It is believed that this class of compounds will yield materials with broad therapeutic applications. In comparison to current methods for the detection and neutralization of bacterial endotoxin (or lipid A), for example, compounds such as the polymyxins, currently employed extensively for the treatment of bacterial sepsis, are heterogeneous mixtures of polypeptides which are difficult to synthesize commercially. The compounds described herein have lipid A binding affinities which are similar to or better than the polymyxins, but are synthesized via an exceptionally short and efficient route.

DETAILED DESCRIPTION OF THE INVENTION

Figure 1:
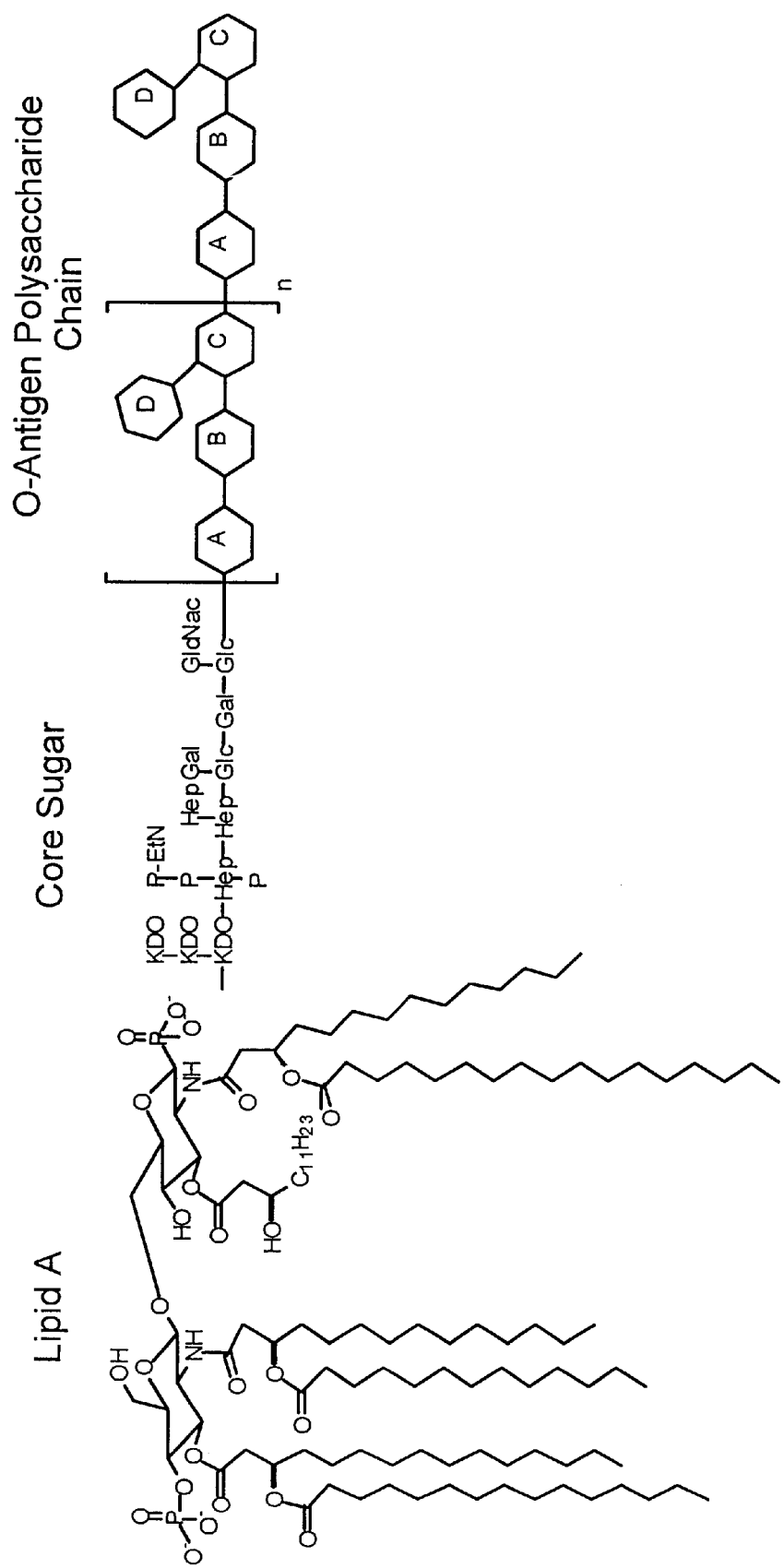
FIG. 1 illustrates the structure of lipopolysaccharide, which includes three domains: lipid A, protein core, and O-antigen polysaccharide chain.

One aspect of the present invention relates to new oligocycloalkanoid compounds according to formula (I) as follows:

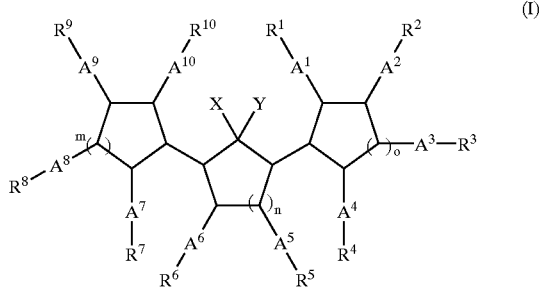

(I)

wherein m, n, and o are independently an integer from 0 to 2;

$A^1$ through $A^{10}$ are independently a direct link, alkylene, alkylene-O—, carbonyl, oxygen, or sulfur;

X and Y are independently hydrogen, hydroxy, alkyl, or in combination an electrophilic group; and $R^1$ through $R^{10}$ are independently hydrogen, hydroxy, alkyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoakylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, or polypeptide, with at least one of $R^1$ through $R^4$ and at least one of $R^7$ through $R^{10}$ being other than hydrogen.

The cycloalkane members can be the same or different, and preferably either a cyclobutane, cyclopentane, or cyclohexane. Although not preferred, individual rings may optionally be cyclopropane or higher cycloalkanes (i.e., cycloheptane, cyclooctane, etc.).

As used herein, "alkyl" (i.e., $CH_3(CH_2)_z$—), "alkylene" (i.e., —$(CH_2)_z$—), "alkenyl" (i.e., $CH_3(CH_2)_z CHCH(CH_2)_z$—), and "alkynyl" (i.e., $CH_3(CH_2)_z CC(CH_2)_z$—) groups, as well as alkoxy, alkenoxy, and alkynoxy groups, can contain be straight or branched chain, and may contain up to about 30 carbon atoms, preferably not more than about 20 carbon atoms, more preferably not more than about 15 carbon atoms. The alkyl, alkylene, and alkenyl groups (or substituent of such group) can be unsubstituted or substituted with halogen, alcohol, thiol, amine, amide, ether, ester, heterocycle, imine, or combinations thereof. When alkyl, alkenyl, or alkynyl substituents are present in other R groups, such as alkylamino, etc., the alkyl, alkenyl, or alkynyl substituents are as described above.

As used herein, "aryl" groups can be either a single ring or fused or multiple rings systems, any of which can be substituted or unsubstituted. Exemplary aryl groups are phenyl or naphthyl, optionally substituted by one or more of alkyl, alkoxy, arylalkyl, arylalkoxy, heterocyclic-alkyl, heterocyclic-alkoxy, OH, alkylamine, alkoxyamine, amido, alkylamido.

When any one of $A^1$ through $A^{10}$ is alkylene-O—, this substituent is present with the alkylene portion bonded directly to the cycloalkane and the oxygen bonded directly to the R group.

When X and Y are in combination an electrophilic group, the electrophilic group can be a keto group or imine group.

Suitable R aryl groups include, without limitation, phenyl, alkylphenyl, alkenylphenyl, alkynylphenyl, alkoxyphenyl, alkenoxyphenyl, alkynoxyphenyl, phenols, or aniline.

Suitable N-, S-, or O-heterocycles include, without limitation, stable 5- to 7-membered monocyclic or stable 7- to 10-membered bicyclic heterocyclic ring, which is either saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure, and may optionally be substituted with one or two moieties selected from alkyl, alkoxy, amine, alkylamine, dialkylamine, amido, alkylamido, sulfide, thiol, $CF_3$, $NO_2$, CN, or halogen. Examples of such heterocycles include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, pyridyl, pyrazinyl, oxazolidinyl, oxazolinyl, oxazolyl, isoxazolyl, morpholinyl, thiazolidinyl, thiazolinyl, thiazolyl, quinuclidinyl, indolyl, quinolinyl, isoquinolinyl, benzimidazolyl, benzopyranyl, benzoxazolyl, furyl, pyranyl, tetrahydrofuryl, tetrahydropyranyl, thienyl, benzoxazolyl, thiamorpholinyl sulfoxide, thiamorpholinyl sulfone, and oxadiazolyl. Also included within the meaning of N-, S-, or O-heterocycles are heteroaryl compounds, that is a heterocyclic moiety which is aromatic in character, such as pyridine. It will be appreciated that the heterocyclic ring described when includes thiazoles, oxazoles, triazoles, thiadiazoles, oxadiazoles, isoxazoles, isothiazols, imidazoles, pyrazines, pyridazines, pyrimidines, triazines and tetrazines which are available by routine chemical synthesis and are stable. The single and double bonds in such heterocycles are arranged based upon the heteroatoms present so that the heterocycle is aromatic (e.g., it is a heteroaryl group).

Suitable amino acids include any L- or D-amino acid, i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Other suitable amino acids include amino acid derivatives such as naphthylalanine or any other known amino acid. Preferably, amino acid moieties are L-amino acids such as glycine, trypthophan, phenylalanine, lysine, glutamine, tyrosine, or combinations thereof which form short polypeptide chains containing preferably not more than about 10 amino acid residues, more preferably not more than about 5 amino acid residues.

Suitable R amino groups include primary amines, secondary amines, and tertiary amines. The amino group can be bonded directly to the cycloalkane (i.e., when A is a direct link) or indirectly through A. For example, suitable secondary amines (i.e., —NHR') include alkylamino groups, alkenylamino groups, alkynylamino groups, arylamino groups, etc. Suitable tertiary amines (i.e., —NR'R") include dialkylamino groups, dialkenylamino groups, dialkynylamino groups, N-alkyl, N-alkenyl amino groups, N-aryl, N-alkyl amino groups, and N-aryl, N-alkenylamino groups, etc.

When A is a carbonyl and R is an amino group of the type described above, it should be apparent to those of skill in the art that, in combination, various amido groups are contemplated within the scope of the present invention.

The R group can also be an acyl (i.e., —COR'), where R' is alkyl, aminoakyl, alkenyl, or aryl. The R group can also be an aroyl (i.e., —CO-aryl-R") where R" is an amine as described above, alkyl, or alkenyl.

When A is oxygen and R is an acyl or aroyl of the type described above, it should be apparent to those of skill in the art that, in combination, various esters are contemplated within the scope of the present invention.

The present invention includes all hydrates, solvates, complexes and prodrugs of the compounds of this invention. Prodrugs are any covalently bonded compounds which release the active parent drug according to Formula I in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-onol tautomers, each tautomeric form is contemplated as being included within this invention whether existing in equilibrium or predominantly in one form.

Synthesis

In general, the oligoalkanoid compounds of the present invention can be prepared by reacting an intermediate compound with an $R^1$ to $R^{10}$ precursor, an oxidizing agent, a reducing agent, or a deprotecting agent, under conditions effective to produce an oligocycloalkanoid compound of the present invention.

The intermediate compound is represented generally by the structure of formula (II) as follows:

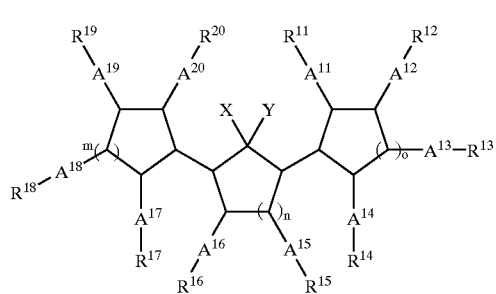

(II)

wherein m, n, and o are independently an integer from 0 to 2; $A^{11}$–$A^{20}$ are independently alkylene, alkylene-O—, carbonyl, oxygen, or sulfur; X and Y are independently hydrogen, hydroxy, alkyl, or in combination an electrophilic group; and $R^{11}$–$R^{10}$ are independenly hydrogen, hydroxy, alkyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoakylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, polypeptide, leaving group, or protecting group, with at least one of $R^{11}$ through $R^{14}$ and at least one of $R^{17}$ through $R^{20}$ being other than hydrogen.

Suitable reducing agents are any known or later developed reducing agents, including without limitation, lithium aluminum hydride, sodium borohydride, sodium cyanoborohydride, lithium tri-tert-butoxyaluminum hydride, borane, diborane, diisobutylaluminum hydride, lithium tri-sec-butyl borohydride, diisopinocampheylborane, dilongifolylborane. Other suitable reducing agents can be utilized according to any synthesis schemes which are known in the art.

Suitable oxidizing agents are any known or later developed oxidizing agents, including without limitation, chromium trioxide, sodium dichromate, potassium permanganate, Dess-Martin periodinane, pyridinium chlorochromate, manganese dioxide, osmium tetroxide, sodium periodate, sodium hypochlorite, hydrogen peroxide, meta-chloroperoxybenzoic acid, trifluoroperoxyacetic acid, potassium ferricyanide, tert-butyl hydroperoxide. Other suitable oxidizing agents can be utilized according to any synthesis schemes which are known in the art.

Suitable deprotecting agents can be any agent which can be utilized, alone or in combination, to remove a protecting group attached to an intermediate molecule for the purpose of inhibiting a particular reaction at a desired site.

An $R^1$ to $R^{10}$ precursor can be any form of $R^1$ to $R^{10}$ which affords the binding of a particular R group to its associated A group (i.e., as in —A—R) or directly to a cycloalkane ring.

More specifically, the compounds of the present invention can be prepared by first preparing the ter-cycloalkane scaffold onto which the —A—R substituents are linked.

Synthesis of a ter-cyclopentane scaffold is achieved according to Scheme 1 as follows.

Scheme 1

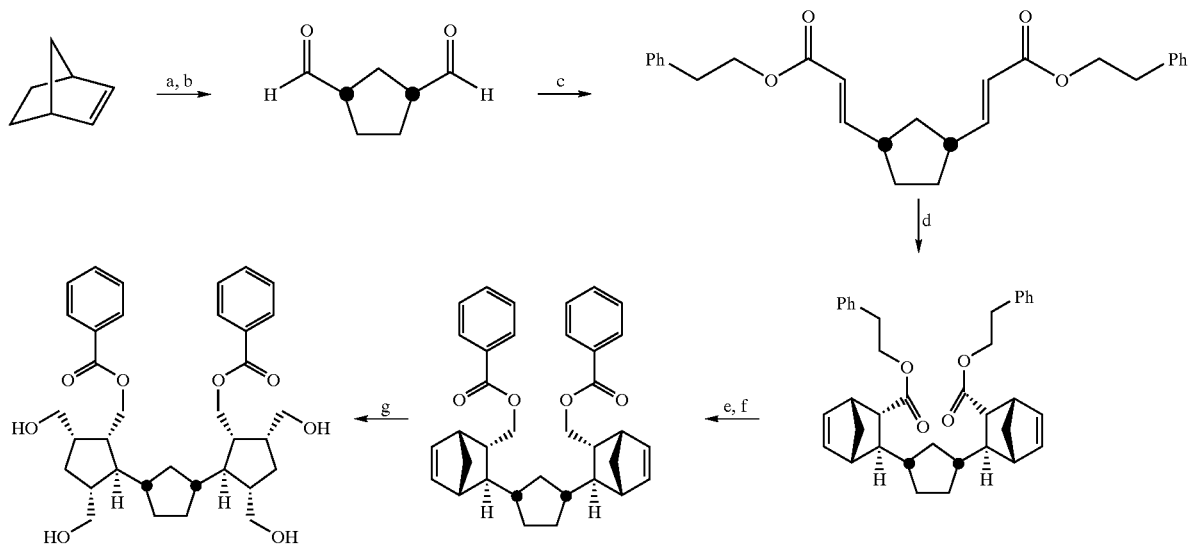

Scheme 1 is carried out by treating norbornylene (Aldrich) with (a) $K_3Fe(CN)_6$, $K_2OsO_4 \cdot 2H_2O$, quinuclidine, $K_2CO_3$, t-BuOH:$H_2O$ 1:1 to yield a diol intermediate which is then (b) treated with $NaIO_4$, THF:$H_2O$ 3:1 at 0° C. to room temperature to yield a dialdehyde; (c) $(iPrO)_2P(O)CH_2C(O)CH_2CH_2Ph$, t-BuOK, THF at 0° C. to room temperature, 2 hr, then the dialdehyde is introduced and the reaction warmed from −78° C. to 4° C. to yield the dieneophile; (d) Diels Alder reaction with $(CH_3)_3Al$ (0.05 eq.) 10 min, then $AlCl_3$ (0.50 eq.), $CH_2Cl_2$ at 0° C., 10 min, then cyclopentadiene (10 eq.) at 4° C. to yield the DA adduct; (e) $LiAlH_4$ (6.0 eq.), THF at room temperature followed by (f) Bz-Cl (3.6 eq.), $Et_3N$ (4.0 eq.), $CH_2Cl_2$ at room temperature (two steps) to yield the dibenzoate-protected DA adduct; and the ter-cyclopentane scaffold is finally assembled at (g) $O_3$, $CH_3OH/CH_2Cl_2$ 1:1 at −78° C., then $NaBH_4$ (10 eq.) at 0° C. to room temperature.

In the Diels-Alder ("DA") reaction between the dienophile (e.g., a hindered dienophile) and the cyclopentadiene, the reaction is catalyzed by a Lewis Acid such as trimethyl aluminum ($Me_3Al$) and aluminum chloride ($AlCl_3$), the use of which is disclosed in Hubbard et al., *J. Org. Chem.* 63(12):4143–4146 (1998), which is hereby incorporated by reference). The benefit of this DA reaction is that it is diastereoselective to favor the endo DA adduct, particularly at lower reaction temperatures (i.e., below room temperature, preferably below 0° C.).

A ter-cyclobutane scaffold can be synthesized according to Scheme 2 as follows:

Cyclobutane-1,3,-dialdehyde (Schwarz et al., *Chem. Ber.* 114(3):990–993 (1981), which is hereby incorporated by reference) is (a) introduced into a reaction mixture containing a substituted phosphonate (prepared as described in Example 2, infra), t-BuOK, THF at 0° C. to room temperature, 2 hr; after addition of dialdehyde, the reaction is warmed from −78° C. to 4° C. to yield the dieneophile; (b) the dienophile is treated with an acyl or ether under a light catalyzed reaction to yield the ter-cyclobutane structure. As shown in Scheme 2, $R^1$ and $R^{10}$ are as described above and n can be 1 or 3 (i.e., central cyclobutane, cyclopentane, or cyclohexane). Undenoted R groups can be the same or different and, for purposes of Scheme 2, can be an alkyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, etc.

An oligocycloalkanoid of the present invention which contains a central cyclohexane ring can be prepared in a manner similar to Scheme 1, except starting with cyclohexane-1,3-dialdehyde or cyclohexane-1,4-dialdehyde (Aldrich).

Having prepared the ter-cycloalkane scaffold, various —A—R substituents can be installed. Typically, the two common intermediates for synthesis of the oligocycloalkanoid compounds of the present invention are the acids (e.g., tetra-acid) and alcohols (e.g., tetra-ol). The tetra-ol can be used to prepare the tetra-acid according to Scheme 3 below.

Scheme 2

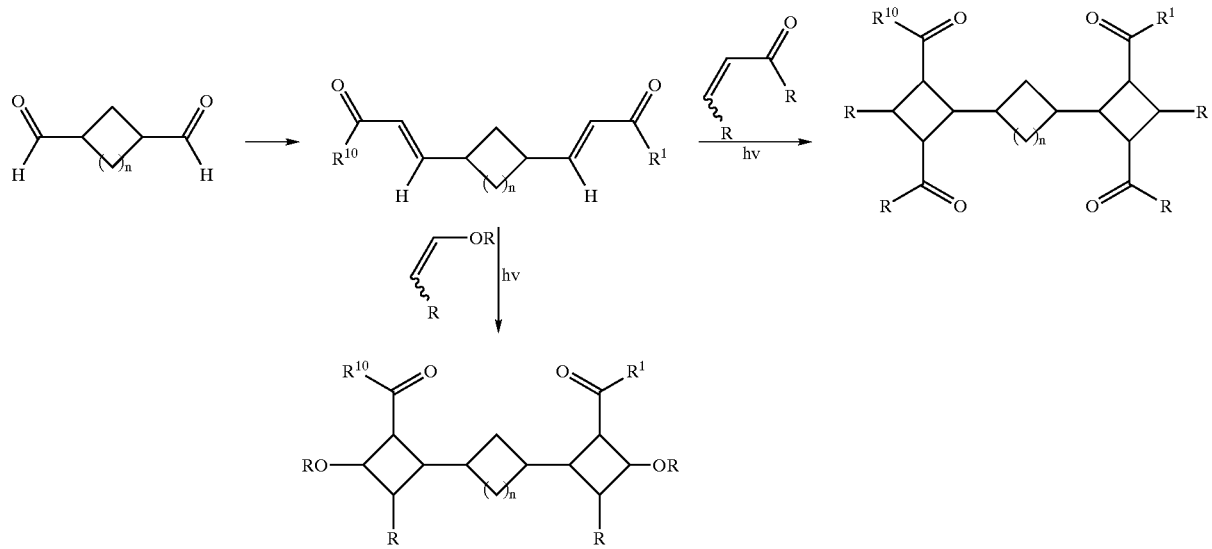

Scheme 3

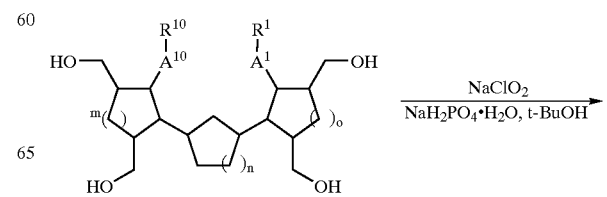

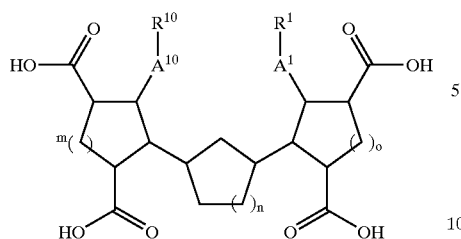

The tetra-ol is treated with NaClO$_2$ and NaH$_2$PO4.H$_2$O in t-butanol to convert the alcohol (i.e., methanol) substituent into a carboxylic acid substituent.

The tetra-acid can then be used to prepare a variety of functional —A—R groups where A is a carbonyl. For example, according to the synthesis scheme 4A, treatment of the tetra-acid with SOCl$_2$ yields an acid chloride intermediate that can then be reacted with alcohols, primary amines, secondary amines, or tertiary amines having R groups as defined above.

Scheme 4A

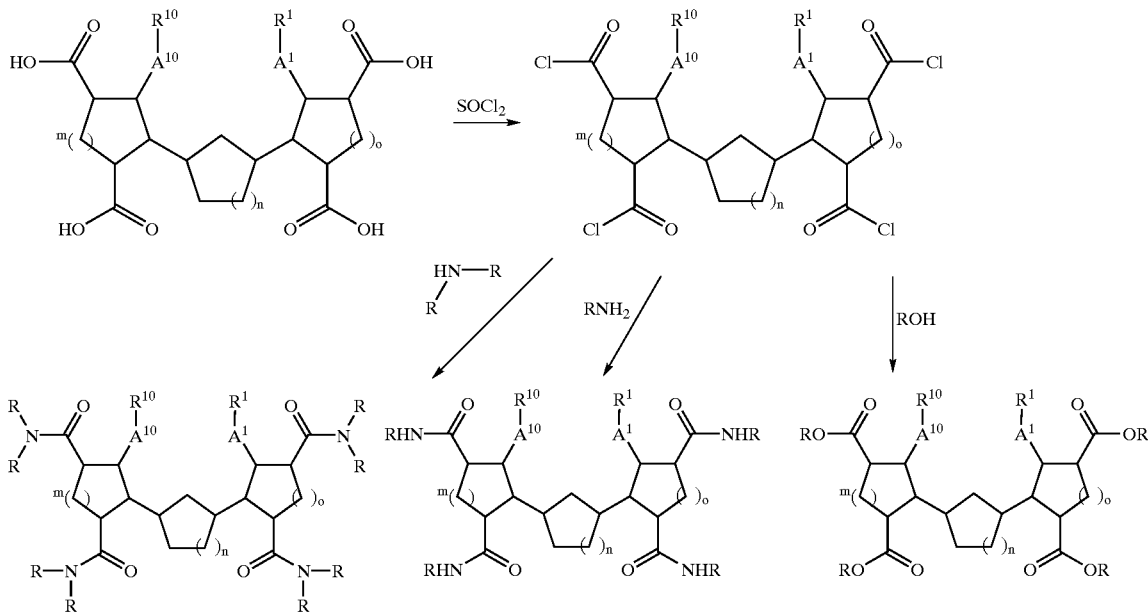

In addition, treatment of the tetra-acid with a diimidazole ketone in CH$_2$Cl$_2$, then a HNRR, where each R group is independently as described above, (e.g., NH(CH$_3$)(OCH$_3$)) to yield an amido group, as shown in synthesis Scheme 4B below.

Scheme 4B

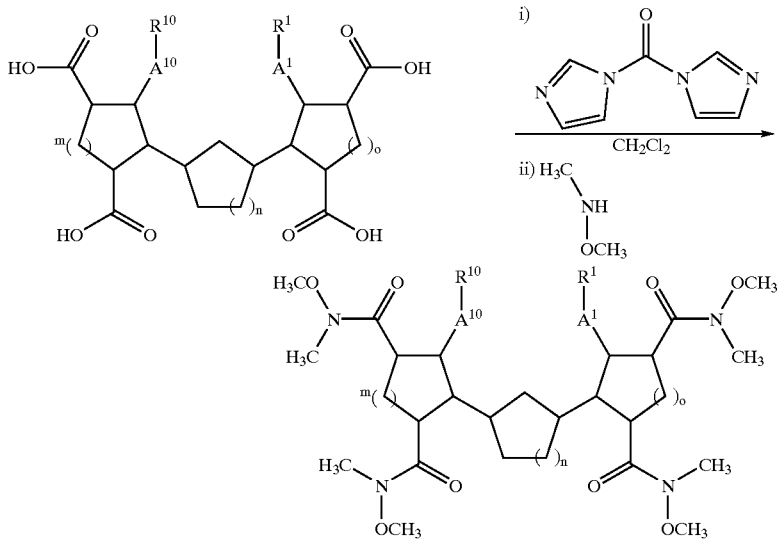

The compound prepared in Scheme 4B can also be used as an intermediate to prepare oligocycloalkanoid compounds of the present invention having a variety of functional —A—R groups where A is O. For example, according to the synthesis scheme 5, treatment of the product from Scheme 4B can be further treated to modify the R group while maintaining A as a carbonyl or it can be converted to form hydroxy substituted cycloalkanes.

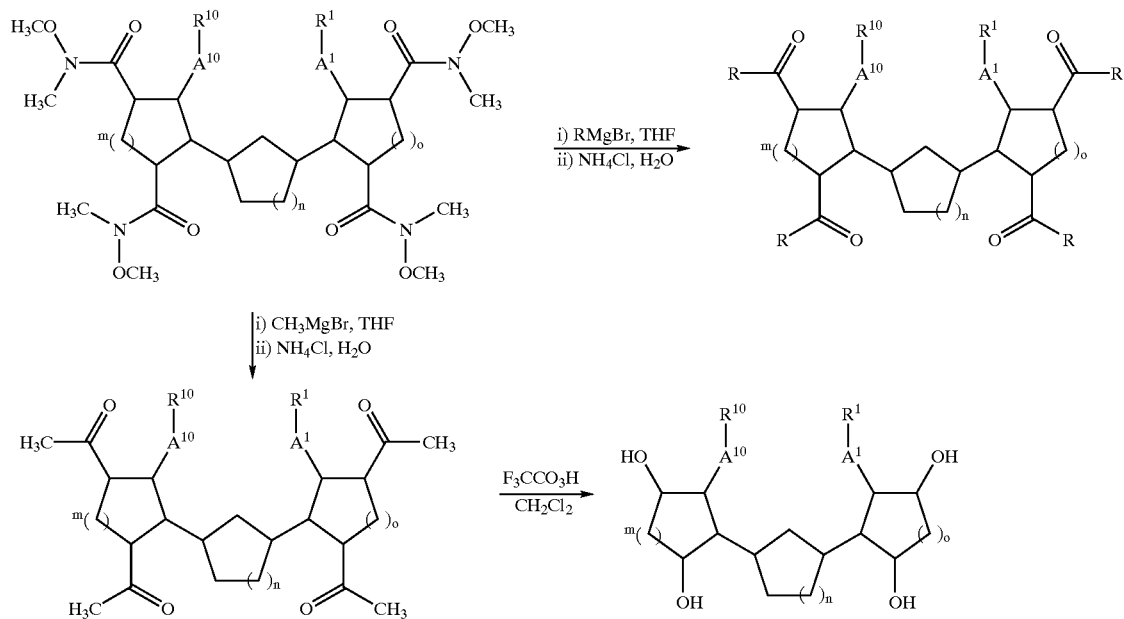

Scheme 5

The product from Scheme 4B can be treated with $CH_3MgBr$ in THF and then ammonium chloride in water to yield a methylacyl —A—R, which is then treated with $F_3CCO_3H$ and $CH_2Cl_2$ to yield the hydroxy substituted oligocycloalkane. The hydroxy substituted oligocycloalkane can then be reacted using conventional schemes to replace the R group for each —A—R where A is oxygen.

Alternatively, the tetra-ol intermediate can be used to prepare a variety of —A—R groups where A is alkyl or alkylene-O— as shown in synthesis scheme 6 below.

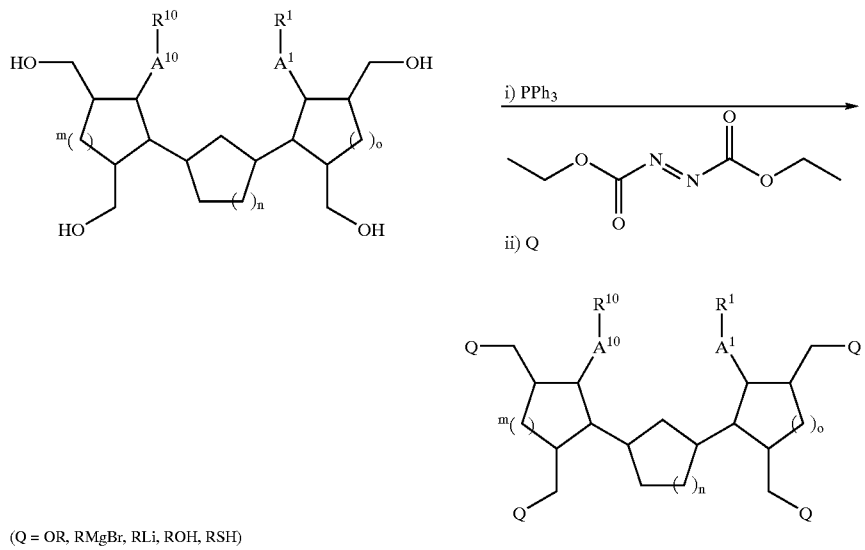

Scheme 6

(Q = OR, RMgBr, RLi, ROH, RSH)

The tetra-ol intermediate is treated with PPh$_3$ and an azide, followed by introduction of Q into the reaction, whereby the hydroxy groups are substituted by Q, where R can be as described above.

Finally, the hydroxy substituted intermediate prepared in Scheme 5 can be used to prepare a variety of —A—R groups where A is S as shown in synthesis scheme 7 below.

Scheme 7

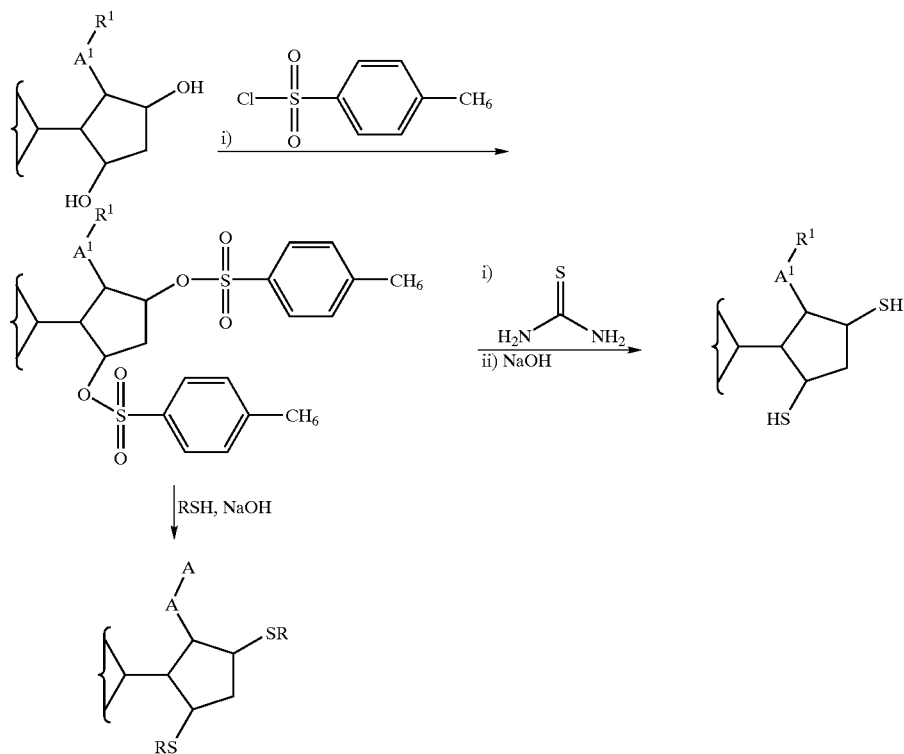

By reacting the hydroxy substituted oligocycloalkanoid compound from Scheme 5 with p-toluene sulfonyl chloride, the sulfonate displaces the proton from the hydroxy group yielding the intermediate, which can be treated in one of two ways. First, the intermediate can be treated with a thiol in NaOH to remove the leaving group and yield sulfide —A—R groups where R is as described above. Second, the intermediate is treated with thiourea to remove the sulfonate leaving group, then NaOH to yield the oligocycloalkanoid compound having a thiol —A—R group, which can then be treated as desired using known thiol reactions.

Optionally, the oligocycloalkanoid compounds of the present invention can be de-symmetrized either with the use of protecting groups or with the use of stereoselective reactions of intermediate compounds to yield asymmetrical linking of —A—R groups. A number of suitable protecting groups can be introduced, including, without limitation, silyl ethers, alkyl ethers, and benzyl ethers (Green et al., *Protective Groups In Organic Synthesis,* John Wiley and Sons, Inc., New York, 2d ed., pp. 413–410 (1991), which is hereby incorporated by reference. Other suitable protecting groups include, without limitation, an amino acid t-butyl carbamate protecting group ("BOC"), amino acid 9-fluorenylmethyl carbamate protecting group, and trialkylsilyl-protected hydroxyethers and esters. After asymmetrical addition of —A—R groups, the protecting groups can then be removed. For example, the amino acid t-butyl carbamate protecting group can be removed with trifluoroacetic acid in methylene chloride, the amino acid 9-fluorenylmethyl carbamate protecting group can be removed with piperidine in dimethylformamide, and a trialkylsilyl-protected hydroxyether or ester can be removed with tetra-n-butylammonium fluoride in tetrahydrofuran.

According to one approach, de-symmetry can be imposed at the —A$^1$—R$^1$ and —A$^{10}$—R$^{10}$ groups as shown in Scheme 8 below.

Scheme 8

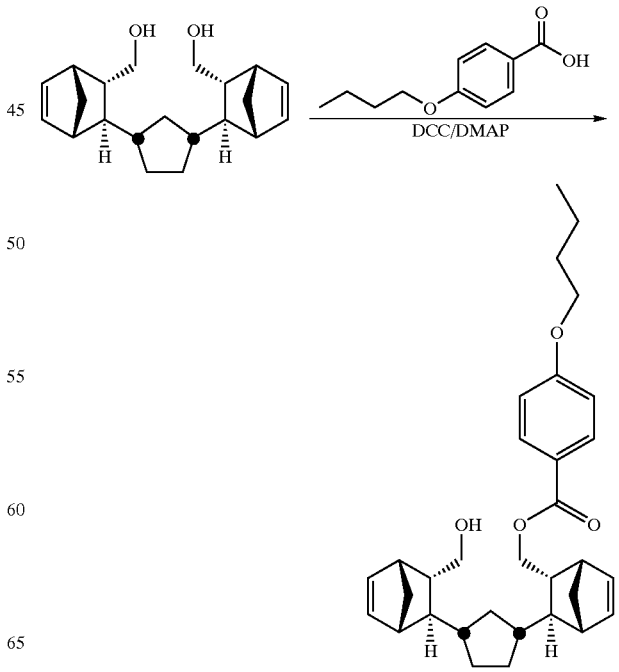

In Scheme 8, the DA adduct (a diol) is treated with a carboxylic acid protective group (containing an ether bond) in DCC/DMAP to protect only —$A^1$—$R^1$. This protecting group can be removed via treatment with boron tribromide in methylene chloride.

Other asymmetrical reaction schemes can be conducted via nucleophilic attack of an anhydride intermediate (as described in Example 13), use of a lactone intermediate (as described in Example 12), protection of a tetra- or di-acid (as described in Example 11).

Once the oligocycloalkanoid compound of the present invention has been prepared, it can be purified using conventional purification procedures, such as high-performance liquid chromatography (HPLC), flash chromatography, or other known procedure, to obtain a product which is preferably at least about 90% pure, more preferably at least about 95% pure, and most preferably at least about 99% pure. Enantiomers can be included in the pure composition or, if desired, the enantiomer(s) of minor proportion can be removed from the enantiomer of major proportion.

Therapeutic Compositions

Once having obtained the desired oligocycloalkanoid of the present invention, it may be administered for various therapeutic purposes. Thus, a further aspect of the present invention relates to a pharmaceutical composition that includes a pharmaceutically acceptable carrier and an oligocycloalkanoid compound according to the present invention.

The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 20 to 75 percent of active compound(s), together with the excipient.

The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The compounds of the present invention may also be administered in injectable dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Compositions within the scope of this invention include all compositions wherein the compound of the present invention is contained in an amount effective to achieve its intended purpose. While individual needs vary, determination of optimal ranges of effective amounts of each component is within the skill of the art. Typical dosages comprise about 0.01 to about 100 mg/kg·body wt. The preferred dosages comprise about 0.1 to about 100 mg/kg·body wt. The most preferred dosages comprise about 1 to about 100 mg/kg·body wt. Treatment regimen for the administration of the compounds of the present invention can also be determined readily by those with ordinary skill in art.

Therapeutic Uses

The oligocycloalkanoid compounds of the present invention are either shown to have or are believed to have significant therapeutic uses, primarily through their interactions with other biological molecules including, without limitation, lipid A, bacterial endotoxin, and various cysteine proteases such as cathepsin K.

One aspect of the present invention relates to the use of oligocycloalkanoid compounds for the treatment of a bacterial infection. According to this aspect of the present invention, an oligocycloalkanoid compound of the present is administered to a patient having a bacterial infection, wherein a bacteriacidally effective amount of the oligocycloalkanoid compound is administered under conditions effective to treat the bacterial infection. In particular, the compounds of the present invention can be used to treat bacterial infections of the type which can lead to septic shock. Thus, a further aspect of the present invention relates to inhibiting or treating septic shock through the administration of an effective amount a oligocycloalkanoid compound of the present invention. In addition, a further aspect of the present invention relates to treating a disease caused by bacterial endotoxin through the administration of an effective amount a oligocycloalkanoid compound of the present invention.

The bacterial endotoxic component of lipopolysaccharide ("LPS") composes a significant fraction of the outer cell wall of all gram-negative bacteria, and is responsible for initiating septic shock or sepsis in higher order vertebrates (i.e., humans and animals). More than 700,000 people in the United States become septic every year (Strauss, *Modern Drug Discovery*, 37–43 (2000), which is hereby incorporated by reference), and due to the high degree of mortality, between 25–70% (Quezado et al., *Trends Biotechnol.* 13:56–63 (1995), which is hereby incorporated by reference), septic shock represents a serious issue that has taken center stage as a dire health problem.

When a host is infected by a normally innocuous pathogen, the immune system is induced to mount an appropriate response. The net result is control of the infection and survival of the host.

However, the pathogenesis of sepsis typically involves the following course of events. Following infections, an inadequate host immune response enables uncontrollable proliferation of the infection, either leading to host destruction or an excessive immune response. The excessive immune response is characteristic of septic shock. In the beginning of septic shock, the symptoms might manifest as flu-like symptoms, such as chills and fever. However, if the immune response is so overwhelming that the host begins to damage self, as well as the foreign entity, organ failure and death can result.

The multitude of symptoms present during sepsis has hampered not only accurately diagnosing the condition in patients (Strauss, *Modem Drug Discovery*, 37–43 (2000), which is hereby incorporated by reference), but has made treatment using conventional chemotherapy problematic. Most chemotherapeutic approaches have focused on neutralizing endotoxin, a component present in all gram-negative bacteria cell walls. Endotoxin, depicted in FIG. 1, is composed of three parts: a negatively charged lipid A portion, a carbohydrate core, and an O-antigen polysaccharide. Lipid A, which has several long-chained aliphatic residues attached to a non-reducing, doubly-phosphorylated glucosamine disaccharide head group, is essential for anchoring the rest of the endotoxin moiety to the outer membrane of the bacterial cell wall (Myers, *Molecular Biology and Biotechnology*, VCH Publishers, New York, pp. 509–511 (1995), which is hereby incorporated by reference). The carbohydrate core is covalently attached to lipid A, via a 3-deoxy-D-manno-octulosonic acid (KDO) residue. The O-antigen chain contains a monosaccharide unit that can repeat 0 to 50 times and protrudes into the surrounding environment. Interestingly, bacteria that possess highly hydrophobic sugars in the O-antigen portion of LPS, like (di-deoxy) sugars, tend to be more pathogenic (Strauss, *Modem Drug Discovery*, 37–43 (2000), which is hereby incorporated by reference).

The conventional chemotherapeutic target to combat septic shock has focused on the recognition and neutralization of the lipid A component of endotoxin. Researchers have shown that lipid A exerts many of the same effects of septic shock when injected into mammals (Ribi et al., *Cancer Res.* 39:4765–4759 (1979), which is hereby incorporated by reference), indicating that lipid A alone is the "pathogenic" component of endotoxin.

A class of cyclic peptides, the polymyxins, have demonstrated both high affinity for lipid A, and also display remarkable cytotoxicity versus a variety of gram-negative bacterial cell lines (Storm, *Ann. Rev. Biochem.* 46:723–763 (1977), which is hereby incorporated by reference). Polymyxin B ("PMB"), comprising B and $B_2$ (Li et al., *J. Am. Chem. Soc.* 121:931–940 (1999), which is hereby incorporated by reference) is used therapeutically as a mixture. PMB derives its cytotoxicity from its ability to not only associate with lipid A (David et al., *Biochimica et Biophysica Acta* 1165:147–152 (1992), which is hereby incorporated by reference), but also allows self-transport through the outer membrane, disrupting the cytoplasmic membrane and resulting in cell death (Vaara, *Microbiol. Rev.* 56:395–411 (1992), which is hereby incorporated by reference). Two derivatives, Polymyxin B nonapeptide and polymyxin B hepapeptide, are much less cytotoxic even though both interact with lipid A or LPS, increasing the permeability of the bacterial cell wall to hydrophobic antibiotics (Vaara et al., *Nature* 303:526–528 (1983); Vaara et al., *Antimicrob. Agents Chemother.* 37:354–356 (1993); Ofek et al., *Antimicrob. Agents Chemother.* 38:374–377 (1994), which are hereby incorporated by reference).

As a result of the differential activities that PMB and its derivatives demonstrate, the interactions can be categorized as either a sublethal interaction or a lethal interaction (Li et al., *J. Am. Chem. Soc.* 121:931–940 (1999), which is hereby incorporated by reference). A sublethal interaction which increases membrane permeability, but it in of itself is not cytotoxic, is typified by the interaction of the above-identified PMB derivatives with gram-negative bacteria. A lethal interaction of the type observed for PMB requires not only association with lipid A, but also self- or mediated transport into the cell, disrupting the cytoplasmic membrane and affording cell death.

Although PMB is an extremely potent antibiotic, with average mean inhibitory concentration (MIC) values residing in the low ug/mL (Vaara et al., *Nature* 303:526–528 (1983)), PMB suffers from a few problems rendering its administration less than ideal. First, as indicated above, PMB is isolated from its natural source as a mixture of polymyxin $B_1$ and polymyxin $B_2$. The structural complexity of PMB has hampered the development of a synthetic route capable of making PMB in large quantities. Second, and perhaps the most serious problem of PMB administration, is its renal toxicity (Kunin, *J. Infect. Diseases* 121:55–64 (1970), which is hereby incorporated by reference), which might be a function of PMB's lethality towards eukaryotic cells (Garrod et al., *Antibiotic and Chemtherapy*, Churchill Livingstone, London, (1981), which is hereby incorporated by reference).

Compounds which are particularly preferred for use in treating or inhibiting septic shock, or otherwise treating a bacterial infection or disease associated with bacterial endotoxin, include, without limitation:

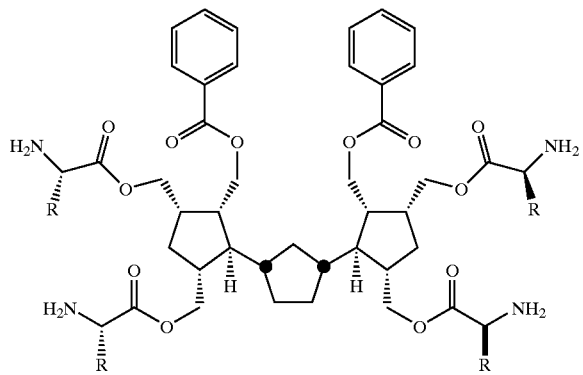

R = CH$_2$Ph or

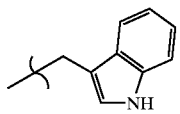

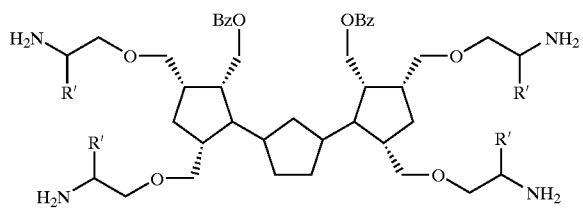

wherein R' is an R group as described above;

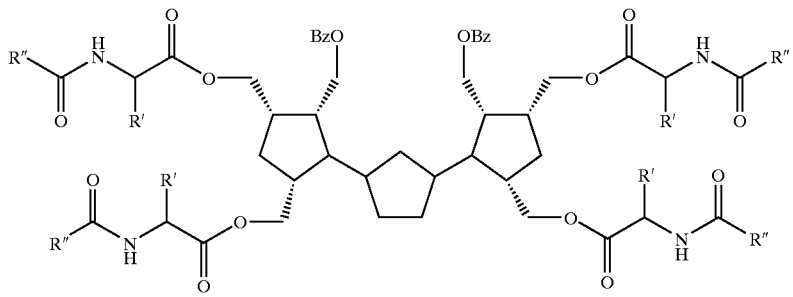

wherein R' and R" are R groups as described above; and

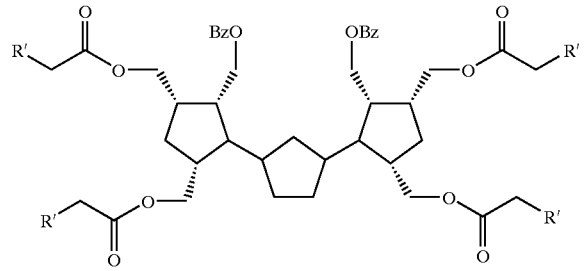

wherein R' is an R group as described above.

As noted infra in the Examples, ter-cyclopentane tetra-tryptophanate, di-benzoate compound of the present invention exhibits a lipid A binding affinity which is greater than the binding affinity of polymyxins. This is promising for activity in treating septic shock, inhibiting endotoxin, or otherwise treating a bacterial infection or disease associated with bacterial endotoxin.

Another aspect of the present invention relates to the use of an oligocycloalkanoid compound of the present invention to inhibit cysteine or serine protease activity, more particularly activity of the cysteine protease cathepsin K. This method is carried out by providing an oligocycloalkanoid compound of the present invention and then introducing the oligocycloalkanoid compound into a system comprising cathepsin K under conditions effective to inhibit cathepsin K. The system can be either an in vitro system or an in vivo system.

Cathepsins are a family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein), which is hereby incorporated by reference. Cathepsin K has been recently expressed, purified, and characterized (Bossard et al., *J. Biol. Chem.* 271:12517–12524 (1996); Drake et al., *J. Biol. Chem.* 271:12511–12516 (1996); Bromme et al., *J. Biol. Chem.* 271: 2126–2132 (1996), which are hereby incorporated by reference).

Cathepsin K has been variously denoted as cathepsin O or cathepsin O2 in the literature. The designation cathepsin K is considered to be the more appropriate one.

Cathepsins function in the normal physiological process of protein degradation in animals, including humans, e.g., in the degradation of connective tissue. However, elevated levels of these enzymes in the body can result in pathological conditions leading to disease. Thus, cathepsins have been implicated as causative agents in various disease states, including but not limited to, infections by *Pneumocystis carinii, Trypsanoma cruzi, Trypsanoma brucei,* and *Crithidia fusiculata;* as well as in schistosomiasis, malaria, tumor metastasis, metachromatic leukodystrophy, muscular dystrophy, amytrophy, and the like (see WO 94/04172 and EP 0 603 873 A1, which are hereby incorporated by reference). Two bacterial cysteine proteases from *P. gingivallis,* called gingipains, have been implicated in the pathogenesis of gingivitis (Potempa et al., *Perspectives in Drug Discovery and Design* 2:445–458 (1994), which is hereby incorporated by reference).

Cathepsin K is believed to play a causative role in diseases of excessive bone or cartilage loss. Bone is composed of a protein matrix in which spindle- or plate-shaped crystals of hydroxyapatite are incorporated. Type I collagen represents the major structural protein of bone comprising approximately 90% of the protein matrix. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodelling at discrete foci throughout life. These foci, or remodelling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive membrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

Several published studies have demonstrated that inhibitors of cysteine proteases are effective at inhibiting osteoclast-mediated bone resorption, and indicate an essential role for a cysteine proteases in bone resorption. For example, Delaisse et al., *Biochem. J.* 192:365 (1980), which is hereby incorporated by reference, discloses a series of protease inhibitors in a mouse bone organ culture system and suggest that inhibitors of cysteine proteases (e.g., leupeptin, Z-Phe-Ala-$CHN_2$) prevent bone resorption, while serine protease inhibitors were ineffective. Delaisse et al., *Biochem Biophys. Res. Commun.* 125:441 (1984), which is hereby incorporated by reference, discloses that E-64 and leupeptin are also effective at preventing bone resorption in vivo, as measured by acute changes in serum calcium in rats on calcium deficient diets. Lerner et al., *J. Bone Min. Res.* 7:433 (1992), which is hereby incorporated by reference, discloses that cystatin, an endogenous cysteine protease inhibitor, inhibits PTH stimulated bone resorption in mouse calvariae.

Other studies also report a correlation between inhibition of cysteine protease activity and bone resorption (Delaisse et al., *Bone* 8:305 (1987); Hill et al., *J. Cell. Biochem.* 56:118 (1994); and Everts et al., *J. Cell. Physiol.* 150:221 (1992), which are hereby incorporated by reference). Tezuka et al., *J. Biol. Chem.* 269:1106 (1994); Inaoka et al., *Biochem Biophys. Res. Commun.* 206:89 (1995); and Shi et al., *FEBS Lett.* 357:129 (1995), which are hereby incorporated by reference, disclose that under normal conditions cathepsin K is abundantly expressed in osteoclasts and may be the major cysteine protease present in these cells.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

Compounds of the present which are believed to be useful in inhibiting cysteine proteases and, more specifically, cathepsin K, include the following:

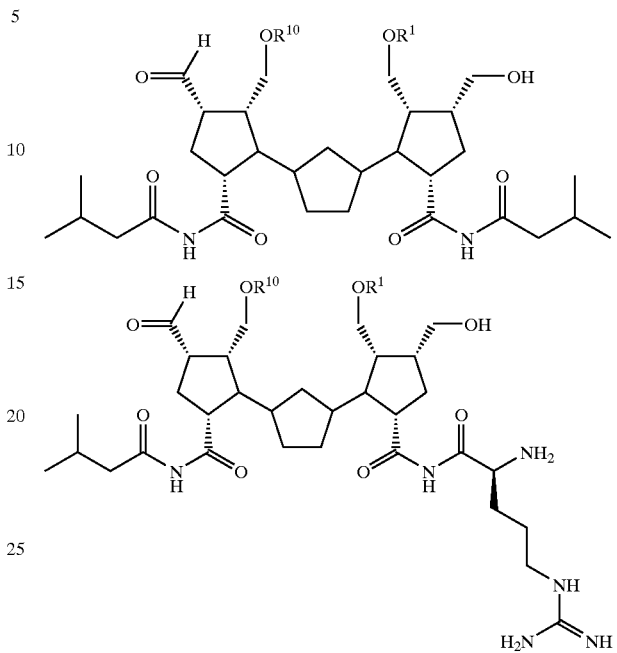

wherein $R^1$ and $R^{10}$ are as set forth above;

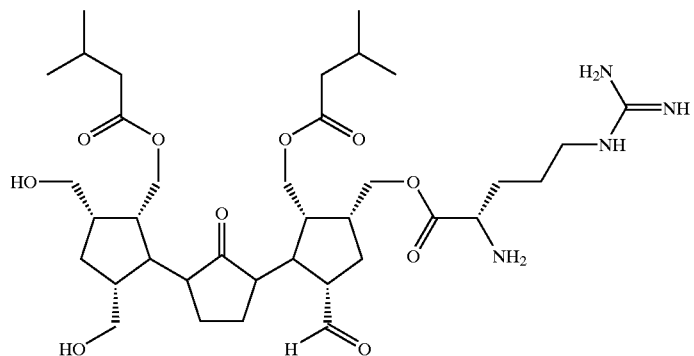

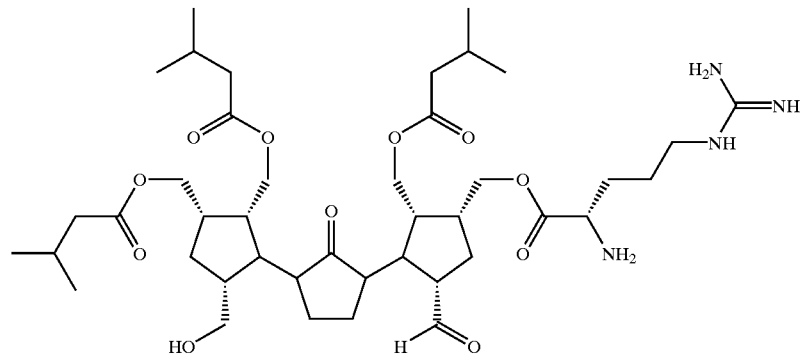

-continued
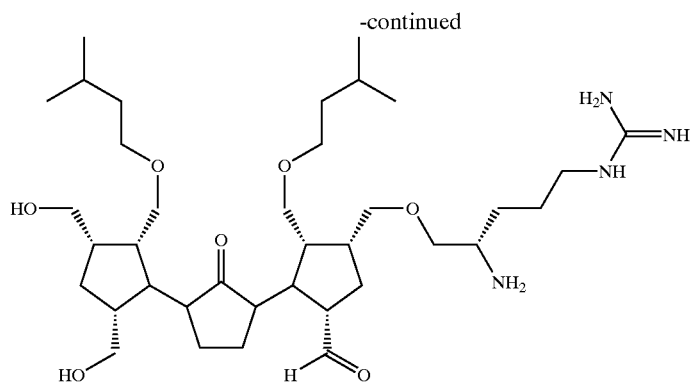
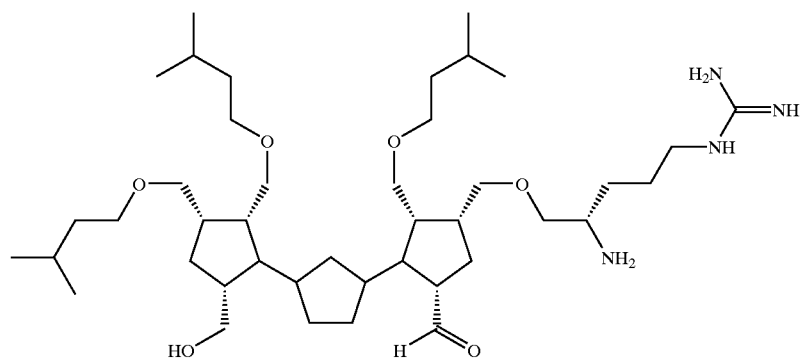
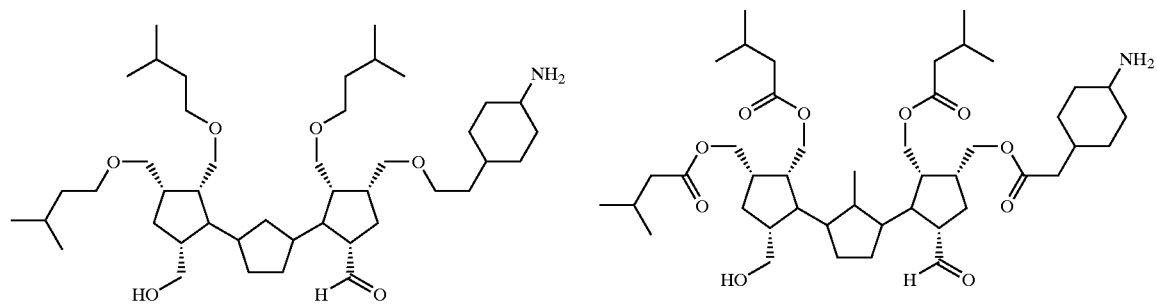
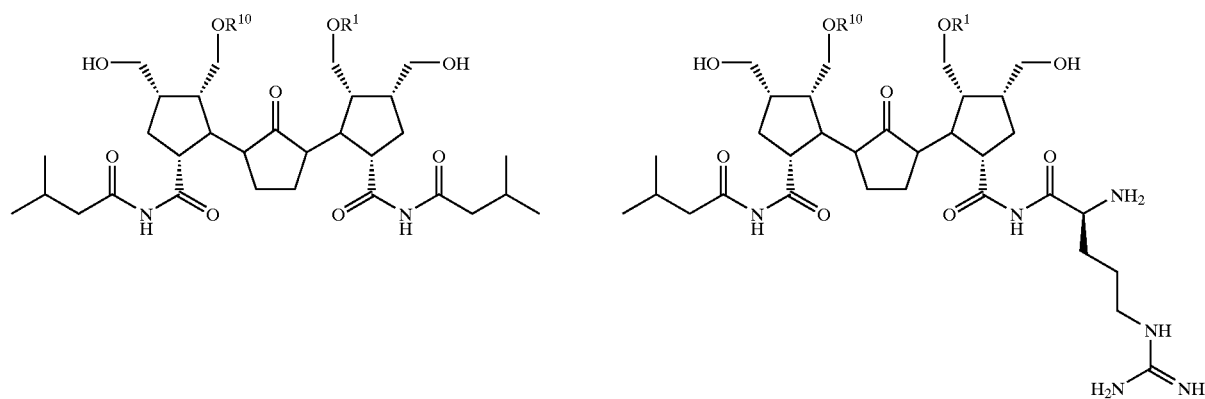
where $R^1$ and $R^{10}$ are as set forth above;

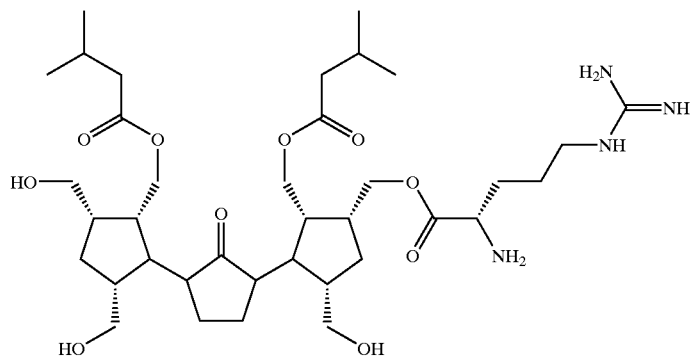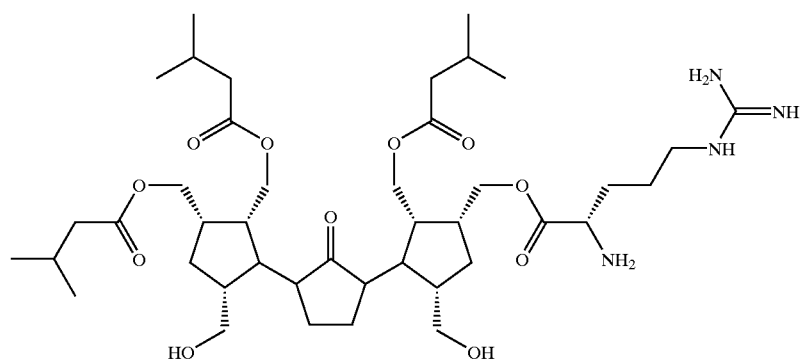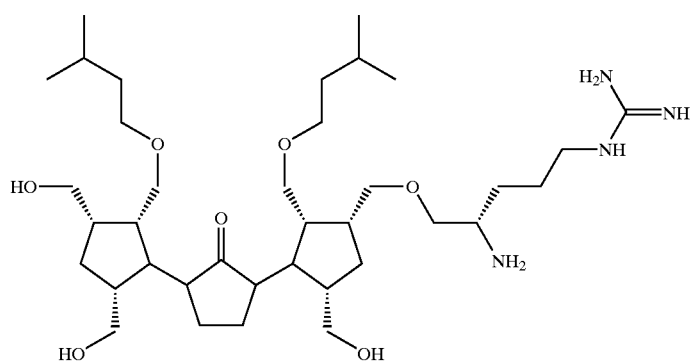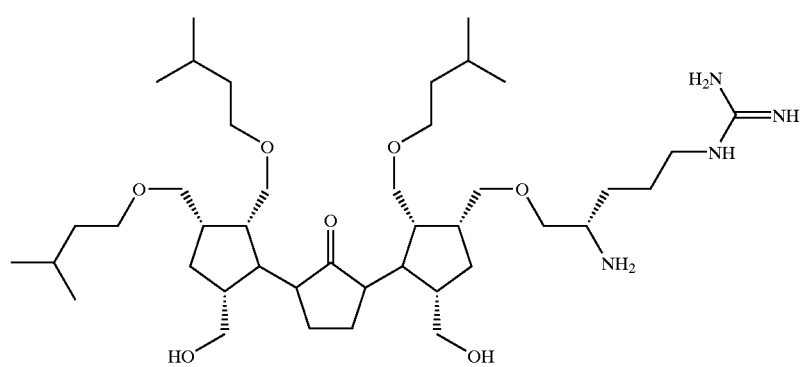

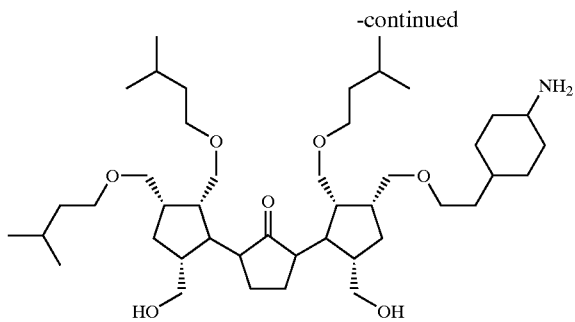
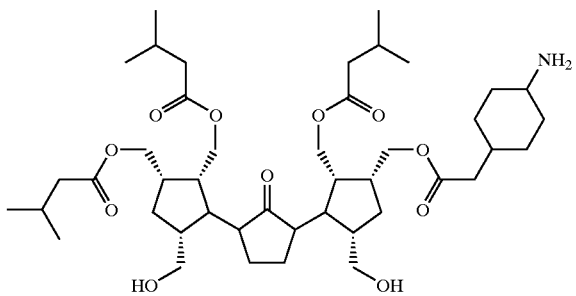

EXAMPLES

The following examples are provided to illustrate embodiments of the present invention, but they are by no means intended to limit its scope.

Example 1

Synthesis of Cyclopentane Dialdehyde

Norbornylene (Aldrich Chemical Co.) was used as a starting material for synthesis of the ter-cyclopentane scaffold. Oxidative cleavage of norbornylene was achieved using the two-step procedure of Sharpless Dihydroxylation, and sodium periodate (NaIO4) cleavage of the resulting diol to give cyclopentane dialdehyde according to the reaction scheme below

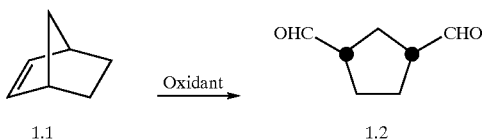

In the first step, norbornylene and the oxidant, which includes $K_3(Fe)_6$, $K_2CO_3$, $MeSO_2NH_2$, Quinuclidine, and $K_2OsO_4 2H_2O$, are introduced into a 1:1 solution of tert-butanol and $H_2O$ at room temperature (Becker et al., *Tetrahedron* 51:1345–1376 (1995), which is hereby incorporated by reference). Cleavage of norbornylene yields a diol, which is then converted to the cyclopentane dialdehyde in a second step.

In the second step, the diol and $NaIO_4$ are introduced into 3:1 solution of THF and $H_2O$ at 0° C. The reaction is allowed to proceed for 12 hours while warming to room temperature. The resulting cyclopentane dialdehyde 1.2 was obtained at a yield of about 63% crude. Because the purity of the crude material was sufficiently high, tedious purification was not necessary. Purification was performed by flash filtration providing a net yield of about 57%.

Example 2

Synthesis of Bis-Dienophilic Ester

The cyclopentane dialdehyde obtained from Example 1 was reacted with a phosphonate ester to prepare a bis-dienophilic ester according to the synthesis scheme below.

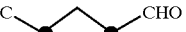

Phenethyl-substituted phosphonate 2.1 was first prepared by introducing triisopropyl phosphite (7.86 g, 37.75 mmol) to a 3-neck round bottom flask equipped with an additional funnel, a short-path distillation apparatus, and an internal thermometer. The phosphite was heated until the internal temperature was stabilized to 120–130° C. The addition funnel was charged with bromoacetate phenylethyl ester (9.17 g, 37.75 mmol). Addition of the bromide to the phosphite was regulated, such that the internal temperature of the reaction remained around 120–130° C. (1.5 hr). During the addition of bromoacetate phenylethyl ester, 2-bromopropane distilled as a clear oil at 60–65° C. After distillation had ceased, the reaction was stirred at 120° C. for 2 hr. The reaction was cooled to room temperature and purified via flash chromatography (silica, 75:25, hexanes: ethyl acetate) to afford phenylethyl-substituted phosphonate 2.1 as a yellow oil (11.37 g, 92% yield).

Phenethyl-substituted phosphonate 2.1 (62.8 g, 191.4 mmol) was dissolved into 0.5 M THF at 0° C. for 30 min. Addition of potassium tert-butoxide (20.06 g, 178.78 mmol) to the phosphonate solution resulted in a canary yellow reaction color. After stirring for 20 min at 0° C., or until the entire base had dissolved in the reaction mixture, the reaction was warmed to room temperature and stirred for an additional 2 hrs. Concurrently, the cyclopentane dialdehyde 1.2 (10.72 g, 85.1 mmol) was dissolved into 2.0 M THF, and cooled to −78° C. for 30 min. The yellow potassium anion of the phenethyl-substituted phosphonate was added via cannula to the aldehyde solution over 1.5 hr. After addition of the anion was complete, the reaction was quickly warmed to 4° C., and stirred overnight at 4° C. The reaction was quenched with water (400 ml), and the resulting layers were separated. The aqueous layer was extracted with ether (4×250 ml). The organics were pooled and washed with a brine solution, dried over $Na_2SO_4$, filtered, and reduced in vacuo to give a yellow oil. Purification of the yellow residue via flash chromatography (silica, 80:20 to 60:40 hexanes:ether) afforded the bis-dienophile ester 2.2 as a pale yellow oil (21.7 g, 61% yield, E,E:E,Z>20:1).

The structure of the bis-dienophile ester 2.2 was confirmed by NMR and MS analysis.

Example 3

Synthesis of Diels-Alder Adduct

The bis-dieneophile 2.2 obtained from Example 2 was reacted with a cyclopentanediene to prepare a Diels-Alder ("DA") adduct according to the synthesis scheme below.

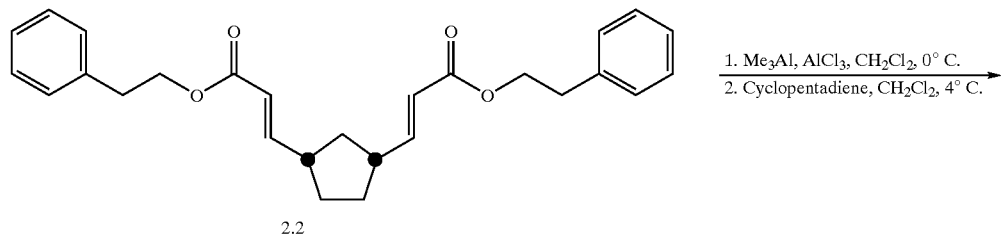

2.2

The bis-dienophile 2.2 (20 g, 47.7 mmol) was dissolved into 0.3 M $CH_2Cl_2$. The resulting (yellow) solution was cooled to 0° C. for 15 min. Addition of $Me_3Al$ (1.19 ml, 2.39 mmol, 2.0 M in hexanes) yielded slight gas evolution, which dissipated upon stirring at 0° C. for an additional 10 min. To the yellow solution, was added $AlCl_3$ (23.8 ml, 23.85 mmol, 1.0 M in $CH_3NO_2$) and the reaction was stirred an additional 5 min at 0° C. Cyclopentadiene (Aldrich Chemical Co.) (31.4 g, 477 mmol, 4.0 M in $CH_2Cl_2$) was added to the colorless solution via an addition funnel dropwise over 30 min. The reaction was warmed to 4° C., and allowed to stir at 4° C. for 12 hr. The reaction was quenched with pyridine (20 ml), and then quickly warmed to room temperature. The resulting thick white slurry was filtered through silica (300 ml), and washed with $Et_2O$ (5×100 ml). The organics were reduced in vacuo. Azeotropic removal of the pyridine and $CH_3NO_2$ was affected by treatment with heptane (4×50 ml) affording a yellow residue. Purification via flash chromatography (silica, 95:5, hexanes:$Et_2O$) afforded the desired DA adduct 3.1 as a yellow oil (18.5 g, 70% yield, endo, endo:endo;exo=18:1). The DA adduct was isolated with about 5% diene impurity.

The structure of the DA-adduct 3.1 was confirmed by NMR and MS analysis.

Example 4

Synthesis of Diol from DA Adduct

The DA adduct 3.1 obtained from Example 3 was converted from the bis-phenylethyl ester to a diol according to the synthesis scheme below.

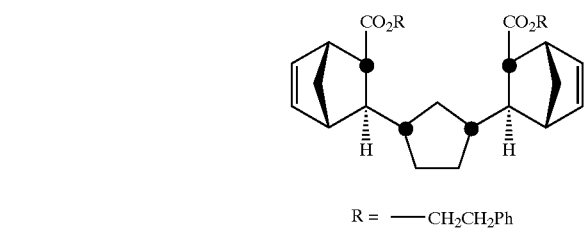

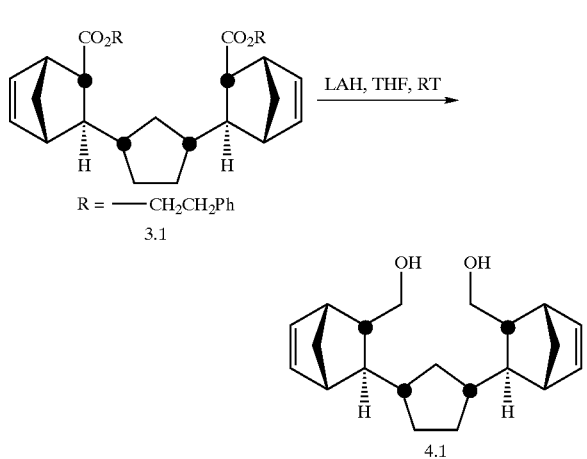

("LAH") (3.6 g, 96.24 mmol) was slurried into 130 ml of THF at room temperature, resulting in slight gas evolution. An addition funnel was charged with the DA adduct with the phenylethyl ester moieties (8.83 g, 16.04 mmol) in 30 ml of THF. The ester was added to the LAH solution over 15 min at room temperature, with vigorous gas evolution. The reaction stirred for 3 hr at room temperature, then quenched sequentially with water (3.6 ml), 15% NaOH aq. solution (3.6 ml), and water (11 ml). The reaction formed a white precipitate and was allowed to stir for 2 hr at room temperature. The reaction contents were filtered through Celite (400 ml), and the pad was washed with ether (5×100 ml). The filtrate was dried over $K_2CO_3$, filtered and reduced in vacuo to give a yellow oil. Purification of the oil via flash chromatography (silica, 66:34 hexanes:ethyl acetate) afforded the diol (2.65 g, 53% yield).

The structure of the diol 4.1 was confirmed by NMR and MS analysis.

Example 5

Protection of Diol and Oxidative Cleavage of Nobornylene Fused Rings

The diol 4.1 obtained from Example 4 was protected with the addition of benzoyl groups according to the scheme set forth below.

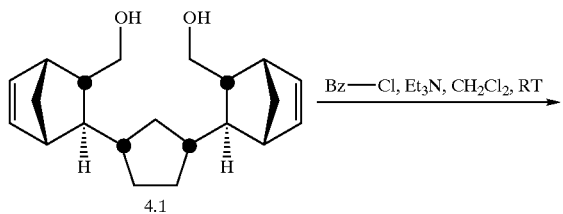

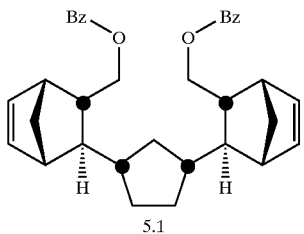

The diol 4.1 (3.1 g, 9.85 mmol) was slurried into 0.2 M $CH_2Cl_2$ at room temperature. Sequential addition of benzoyl chloride (5.0 g, 35.7 mmol), and $Et_3N$ (5.4 ml, 39.36 mmol) at room temperature to the slurry caused the reaction to become yellow and homogeneous. After stirring for 30 min at room temperature, the reaction began to form a white precipitate. According to TLC analysis, SM was consumed within 3 hr. The reaction was quenched with water (25 ml), and poured into ether (100 ml). The layers were separated, and the organic layer was washed sequentially with water (2×100 ml), buffered aq. solution of $NaH_2PO_4 \cdot H_2O$/concentrated HCl (pH=2, 2×100 ml), water (1×100 ml), sat aq $Na_2CO_3$ (2×100 ml), and sat aq. NaCl solution (100 ml). The organic layer was dried over $Na_2SO_4$, filtered, and reduced in vacuo to afford a tan oil. Purification of the oil via flash chromatography (silica, 95:5 hexanes:ether) yielded the di-benzoate compound 5.1 (4.6 g, 91% yield) as a thick colorless oil.

The structure of the di-benzoate compound 5.1 was confirmed by NMR and MS analysis.

The resulting di-benzoate was subsequently subjected to oxidative cleavage of the norbornylene fused rings with ozone according to the reaction scheme below.

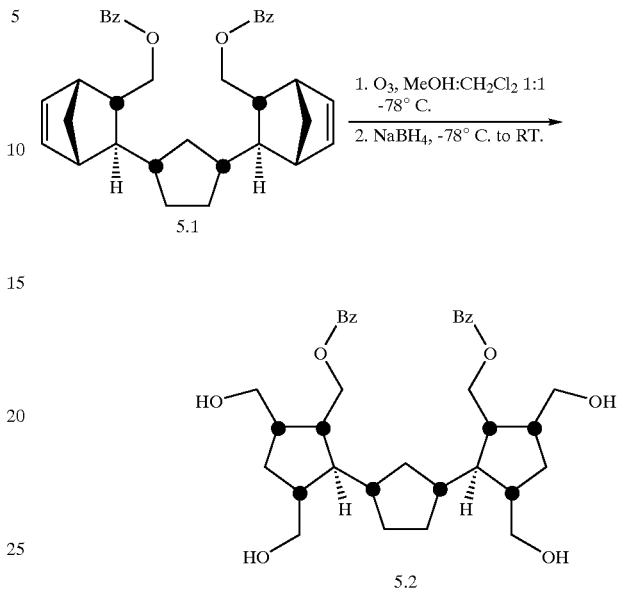

The di-benzoate 5.1 (4.4 g, 8.42 mmol) was dissolved into 0.1 M solution of 1:1 $CH_2Cl_2$:MeOH, and cooled to −78° C. for 10 min. Ozone ($O_3$) was bubbled through the solution until the reaction mixture became deep blue in color (10 min), then $O_3$ treatment continued for an additional 5 min. $O_3$ bubbling was discontinued, and $O_2$ bubbling was commenced to remove excess $O_3$. Once the blue color dissipated, the reaction was warmed to 0° C. for 10 min. $NaBH_4$ (4.46 g, 118 mmol) was added in 1 g portions, over 1 hr. Each addition yielded vigorous gas evolution. After all the $NaBH_4$ had been added, the reaction was allowed to slowly warm to room temperature over 30 min. The reaction was stirred for 4 hr at room temperature. The reaction was quenched with 10% aq. HCl, until the pH was about 1. The contents were diluted with ethyl acetate, and the layers were separated. The aqueous layer was extracted with ethyl acetate (4×100 ml). The organic extracts were combined and washed sequentially with water (100 ml), sat. aq. $Na_2CO_3$ (2×100 ml), and sat. aq NaCl (100 ml). The organics were dried over $Na_2SO_4$, filtered, and reduced in vacuo to afford an opaque solid. The residue was treated with MeOH (3×100 ml). The resulting white solid was purified via flash chromatography (silica, 90:9:1 $CH_2Cl_2$:MeOH:acetic acid) to afford the ter-cyclopentane tetra-ol 5.2 intermediate (2.95 g, 60% yield) as a white solid after azeotropic removal of residual acetic acid with heptane.

The structure of the ter-cyclopentane tetra-ol intermediate was confirmed by NMR and MS analysis.

Example 6

Synthesis of ter-Cyclopentane Hexa-benzoate and Solution Structure Thereof

Using the ter-cyclopentane tetra-ol synthesized as described in Example 5, a ter-cyclopentane hexa-benzoate was prepared in order to determine the solution structure (i.e., symmetry) of the ter-cyclopentane structure. The ter-cyclopentane hexa-benzoate was prepared according to the synthesis scheme below.

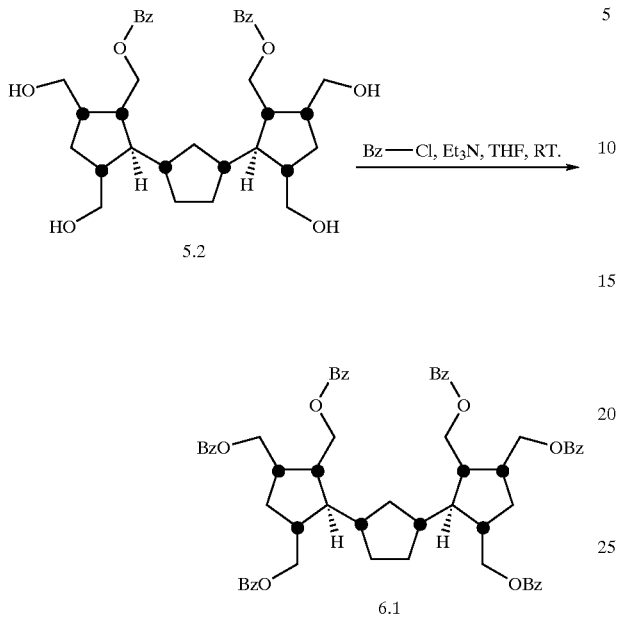

The ter-cyclopentane tetra-ol (0.75 g, 1.25 mmol) was dissolved into 0.1 M THF at room temperature. Added benzoyl chloride (0.88 ml, 7.55 mmol) to the tetra-ol solution, and stirred at room temperature for 5 min, before adding Et$_3$N (1.08 ml, 7.75 mmol). After stirring at room temperature for 10 min, reaction became slightly cloudy. After stirring for 24 hr at room temperature, reaction was diluted with ethyl acetate and poured into water (20 ml). The layers were separated, and the aqueous layer was extracted with ethyl acetate (3×20 ml). The organic extracts were pooled, and washed sequentially with 10% aq HCl solution (10 ml), water (10 ml), and sat aq Na$_2$CO$_3$ (10 ml). The layers were separated and the organic layer was dried over Na$_2$SO$_4$, filtered, and reduced in vacuo to afford a golden yellow residue. Purification of the residue via flash chromatography (silica, 75:25 hexanes:ethyl acetate) afforded the ter-cyclopentane hexa-benzoate (0.76 mg, 60% yield) as an off-white solid.

A series of 1D and 2D NMR experiments were performed in order to determine the solution structure(s) of the ter-cyclopentane hexa-benzoate 6.1. The purpose of the solution structure was to determine the torsional angles between the central cyclopentane ring and those on the periphery was approximately 180°, which would be the ideal case, shown at 6.1-A. However, if one of the aforementioned torsional angles were equal to 60° or a gauche conformation, then the solution structure would be closer to 6.1-B, or 6.1-C if both torsional angles were 60°. The primary focus in analyzing the data was to assign the four protons that compose the torsional angles in question and determine the value of the angle(s). In addition, the full assignment of all protons on the scaffold system aided in the determination of the solution structure(s) of the ter-cyclopentane hexa-benzoate 6.1.

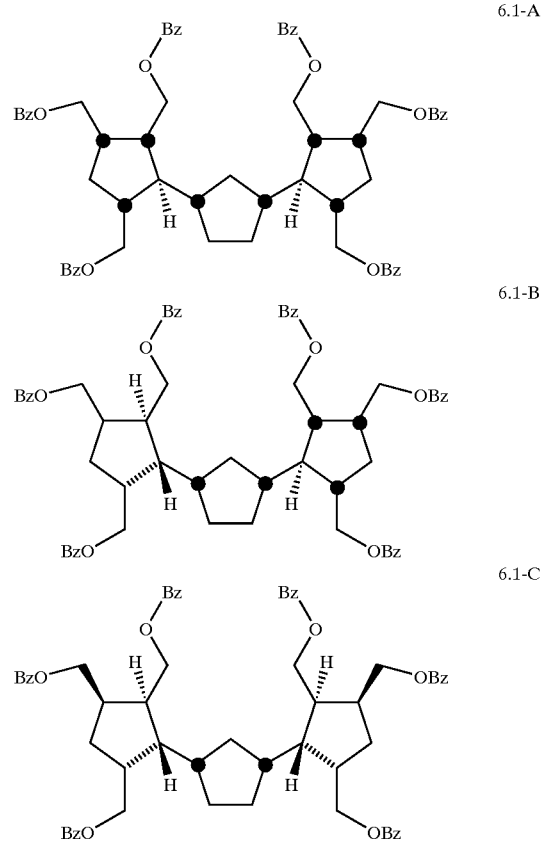

The initial $^1$H and $^{13}$C NMR proved to be very interesting. The $^1$H NMR was helpful in determining the integration for the peaks present in the spectrum. From the $^1$H spectrum of ter-cyclopentane hexa-benzoate, the molecule possesses three types of magnetically distinct protons. The group of resonances from 7–8.5 ppm results from the methines attached to the six aromatic rings. The cluster of peaks from 4–5 ppm is indicative of protons that are adjacent to the benzoyl group. Finally, the peaks from 1–2.8 ppm represent the cycloalkanyl protons. (For an encyclopedic list of chemical shifts of protons on a carbon adjacent to functional group, see Silverstein et al., *Spectrometric Identification of Organic Compounds*, John Wiley and Sons, Inc., New York, 5$^{th}$ Ed., pp. 208–220 (1991), which is hereby incorporated by reference).

The $^{13}$C NMR, which can be used to test symmetry, showed 36 carbon signals, out of a possible 62. If the molecule was symmetric, then the carbon would have shown 33 signals. Therefore, 36 signals indicated that the molecule is highly symmetrical, but not entirely so.

A series of 2-D NMR experiments was also performed on the ter-cyclopentane hexa-benzoate. The first experiment executed was a Heteronuclear Single Quantum Coherence (HSQC) experiment, which yielded information regarding H-C coupling and was invaluable in determining the number of protons present for a given resonance. The HSQC, like the $^{13}$C NMR spectrum, indicated that the ter-cyclopentane hexa-benzoate assumes a conformation(s) with a high degree of symmetry.

The second experiment was a Double Quantum Filtered-COSY ("DQF-COSY") yielded connectivity data via spinspin coupled protons, and allowed for the quantification of torsional angles by measuring coupling constants. The cross peaks for the four protons positioned at the C—C bonds between the central cyclopentane ring and the adjacent cyclopentane rings were nicely resolved and relatively isolated from neighboring crosspeaks. A horizontal slice of this crosspeak revealed that the coupling constant was 14 Hz +/−2 Hz, which would yield a dihedral angle of 180°. If the dihedral angle were 0°, then the Karplus correlation (Gunther, *NMR Spectroscopy*, John Wiley and Sons, Inc., Chichester, 2$^{nd}$ Ed., p. 115 (1996), which is hereby incorporated by reference) would have predicted a coupling constant of 8–12 Hz. This value is somewhat lower than the observed value of 14. Therefore, it is highly unlikely that the dihedral angle of was roughly 180°, as originally modeled.

A third experiment was a two-dimensional homonuclear Nuclear Overhauser Effect Spectrum ("NOESY"), which has become an invaluable technique in determining the relative configuration of protons, in medium and large molecules. The presence of NOE's have been used to not only determine the diastereoselectivity of reactions (DeShong et al., *J. Org. Chem.* 47:4397–4403 (1982), which is hereby incorporated by reference), but also NOESY data has been used to generate solution structures of natural products (Graden et al., *J. Am. Chem. Soc.* 106:1119 (1984), which is hereby incorporated by reference). Therefore, NOESY spectroscopy would provide definitive information regarding the orientation of the terminal cyclopentane rings, with respect to the internal ring of the ter-cyclopentane hexa-benzoate. A series of NOESY spectra, with four different mixing times, was obtained. From the COSY data, it was abundantly clear that the ter-cyclopentane system most closely resembled 6.1-A; however, the NOESY data was needed for confirmation. The NOE peaks which were generated could have been produced by only the structure having conformation 6.1-A.

In conclusion, a combination of 2-D NMR techniques and modeling confirmed that the preferred conformation of 6.1 is one in which the torsional angles around the central cyclopentane ring prefer to be 180°.

Example 7

Synthesis of Water Soluble ter-Cyclopentane Tetra-Amino Acid Derivatives

Starting with the ter-cyclopentane tetra-ol 5.2 prepared according to Example 5, ter-cyclopentane tetra-amino acid derivatives were prepared after initial modeling with the tetra-glycinate revealed surface complimentarily with the disaccharide portion of lipid A. The synthesis scheme is represented below.

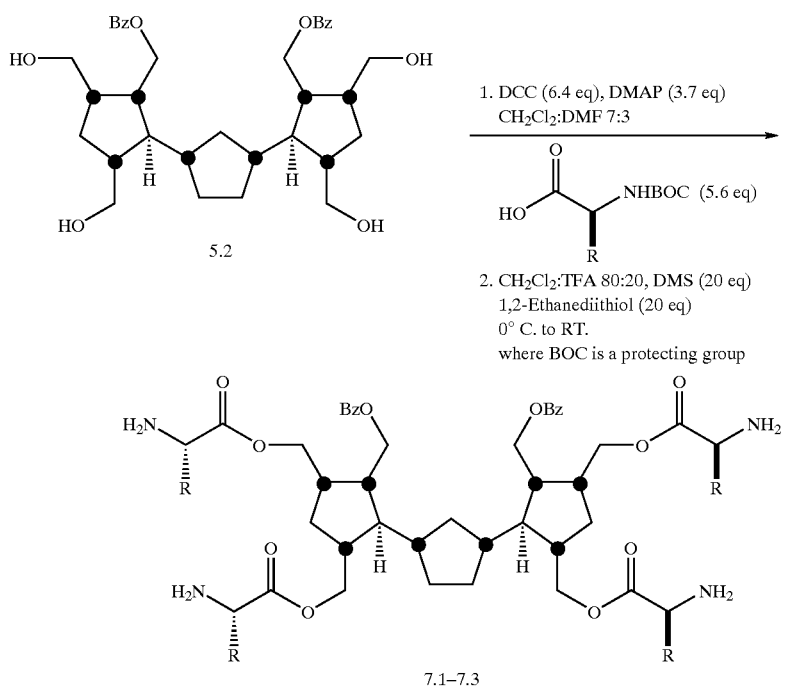

Table 1 below indicates the particular amino acid derivative prepared, the product designation thereof, and the yield from the ter-cyclopentane tetra-ol 5.2.

TABLE 1

Amino Acid Derivatives of ter-Cyclopentane Tetra-ol (5.2)

| Entry | Amino Acid R = | Product | Yield from 5.2 |
|---|---|---|---|
| 1 | —H(Gly) | 7.1 | 30% |
| 2 | —CH$_2$Ph(Phe) | 7.2 | 22% |
| 3 | (Trp) | 7.3 | 20% |

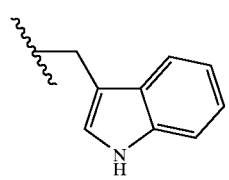

Tetra-glycinate derivative
The ter-cyclopentane tetra-ol 5.2 (0.123 g, 0.206 mmol) was dissolved into 0.05 M solution of 70:30 CH$_2$Cl$_2$:DMF at RT. Sequential addition of BOC-glycine (0.203 g, 1.16 mmol), DCC (0.272 g, 1.32 mmol), and DMAP (0.093 g, 0.762 mmol) caused the formation of a white precipitate to occur. The reaction was allowed to stir at RT for 18 hr. The reaction contents were filtered through Celite, and the pad was washed with ethyl acetate (4×3 ml). The combined organics were washed sequentially with water (2×5 ml), sat. aq. NaHCO$_3$ solution (3×5 ml), and sat. aq. NaCl solution (10 ml). The organics were dried over Na$_2$SO$_4$, filtered, and reduced in vacuo affording an orange-yellow residue, that was used without further purification. The crude BOC-protected tetra-glycinate was dissolved into 2.5 ml of CH$_2$Cl$_2$ at 0° C. Added 1,2-ethanedithiol (0.264 ml, 3.15 mmol) and dimethyl sulfide (DMS, 0.231 ml, 3.15 mmol) to the CH$_2$Cl$_2$ solution, and stirred at 0° C. for 20 min. The dropwise addition of trifluoroacetic acid (TFA, 0.5 ml) to the reaction mixture caused slight gas evolution to occur. The reaction was allowed to stir for 1 h at 0° C., then warmed to RT and stirred for an additional hr. The reaction contents were reduced in vacuo to afford a yellow oil. The residue was purified via reverse phase HPLC using gradient elution, 90:10 0.1% TFA in water:0.1% TFA in CH$_3$CN to 100% of 0.1% TFA in CH$_3$CN solution to give 7.1 as a white solid (47 mg, 30% yield).

NMR and mass-spectometry analyses confirmed the identity of the tetra-glycinate ter-cyclopentane 7.1.

Tetra-phenylalaninate Derivative

The ter-cyclopentane tetra-ol 5.2 (0.103 g, 0.173 mmol) was dissolved into 0.05 M solution of 70:30 CH$_2$Cl$_2$:DMF at RT. Sequential addition of BOC-L-phenylalanine (0.257 g, 0.968 mmol), DCC (0.228 g, 1.11 mmol), and DMAP (0.078 g, 0.64 mmol) caused the formation of a white precipitate to occur. The reaction was allowed to stir at RT for 18 hr. The reaction contents were filtered through Celite, and the pad was washed with ethyl acetate (4×3 ml). The combined organics were washed sequentially with water (2×5 ml), sat. aq. NaHCO$_3$ solution (3×5 ml), and sat. aq. NaCl solution (10 ml). The organics were dried over Na$_2$SO$_4$, filtered, and reduced in vacuo affording an orange-yellow residue, that was used without further purification. The crude BOC-protected tetra-phenylalaninate was dissolved into 2.0 ml of CH$_2$Cl$_2$ at 0° C. Added 1,2-ethanedithiol (0.094 ml, 2.54 mmol) and dimethyl sulfide (DMS, 0.186 ml, 2.54 mmol) to the CH$_2$Cl$_2$ solution, and stirred at 0° C. for 20 min. The dropwise addition of trifluoroacetic acid (TFA, 0.5 ml) to the reaction mixture caused slight gas evolution to occur. The reaction was allowed to stir for 1 h at 0° C., then warmed to RT and stirred for an additional 18 hr. The reaction contents were reduced in vacuo to afford a yellow oil. The residue was purified via reverse phase HPLC using gradient elution, 90:10 0.1% TFA in water:0.1% TFA in CH$_3$CN to 100% of 0.1% TFA in CH$_3$CN solution to give 7.2 as a white solid (33 mg, 22% yield).

NMR and mass-spectometry analyses confirmed the identity of the tetra-phenylalaninate ter-cyclopentane 7.2.

Tetra-tryptophaninate Derivative

The ter-cyclopentane tetra-ol 5.2 (0.103 g, 0.174 mmol) was dissolved into 0.05 M solution of 70:30 CH$_2$Cl$_2$:DMF at RT. Sequential addition of BOC-L-tryptophan (0.297 g, 0.975 mmol), DCC (0.229 g, 1.11 mmol), and DMAP (0.078 g, 0.64 mmol) caused the formation of a white precipitate to occur. The reaction was allowed to stir at RT for 18 hr. The reaction contents were filtered through Celite, and the pad was washed with ethyl acetate (4×3 ml). The combined organics were washed sequentially with water (2×5 ml), sat. aq. NaHCO$_3$ solution (3×5 ml), and sat. aq. NaCl solution (10 ml). The organics were dried over Na$_2$SO$_4$, filtered, and reduced in vacuo affording an off white residue, that was used without further purification. The crude BOC-protected tetra-tryptophaninate was dissolved into 3.3 ml of CH$_2$Cl$_2$ at 0° C. Added 1,2-ethanedithiol (0.348 ml, 4.13 mmol) and dimethyl sulfide (DMS, 0.302 ml, 4.12 mmol) to the CH$_2$Cl$_2$ solution, and stirred at 0° C. for 20 min. The dropwise addition of trifluoroacetic acid (TFA, 0.5 ml) to the reaction mixture caused slight gas evolution to occur. The reaction was allowed to stir for 1 h at 0° C., then warmed to RT and stirred for an additional 18 hr. The reaction contents were reduced in vacuo to afford a yellow oil. The residue was purified via reverse phase HPLC using gradient elution, 90:10 0.1% TFA in water:0.1% TFA in CH$_3$CN to 100% of 0.1% TFA in CH$_3$CN solution to give 7.3 as a white solid (55 mg, 20% yield).

NMR and mass-spectometry analyses confirmed the identity of the tetra-tryptophaninate ter-cyclopentane 7.3.

The various ter-cyclopentane tetra-amino acid compounds were purified using standard HPLC purification. Products 7.1 and 7.3 were remarkably soluble in water, even at concentrations in the low millimolar range. Product 7.1 required the addition of 4% DMSO to achieve water solubility.

Example 8

Binding Affinity of ter-Cyclopentane Tetra-Amino Acid Derivatives for Lipid A, Glucose, and Glucosamine Simple sugars such as glucose and glucosamine, as well as more complex liposaccharides like lipid A, are very weak absorbers of ultraviolet light; therefore, we measured the affinities of 7.1–7.3 for lipid A and related compounds by UV titration.

A 600 microliter, 0.9 $\mu$M solution of the ter-cyclopentane tetra-amino acid derivative in water (pH=5.0) or phosphate-buffered saline (PBS, pH=7.4) was allowed to equilibrate in a 1.0-ml masked wall UV cell at ambient temperature (22° C.), in a Shimadzu 1600-PC UV spectrophotometer. Tryptophan indole absorbance was monitored at 279.4 nm to ensure a completely equilibrated solution had been obtained. Aliquots of 2.5 to $\mu$M diphsophoryl Lipid A (from *Salmonella minnesota* Re-595, Sigma Chemical Co., used without further purification), glucose, or glucosamine were sequentially added to the cuvette. After each addition, the solution was allowed to equilibrate for a minimum of 5 minutes, then scanned for absorbance 550–220 nm.

Figure 2:
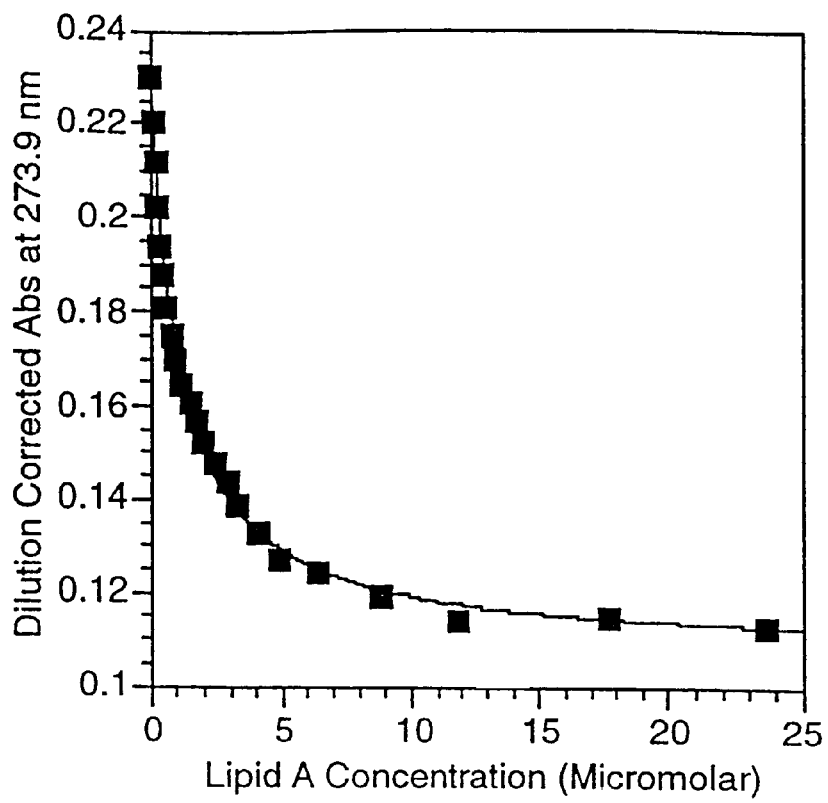
FIG. 2 is a graph illustrating the UV titration of the ter-cyclopentane tetra-phenylanalinate derivative in PBS solution with lipid A.
Figure 3:
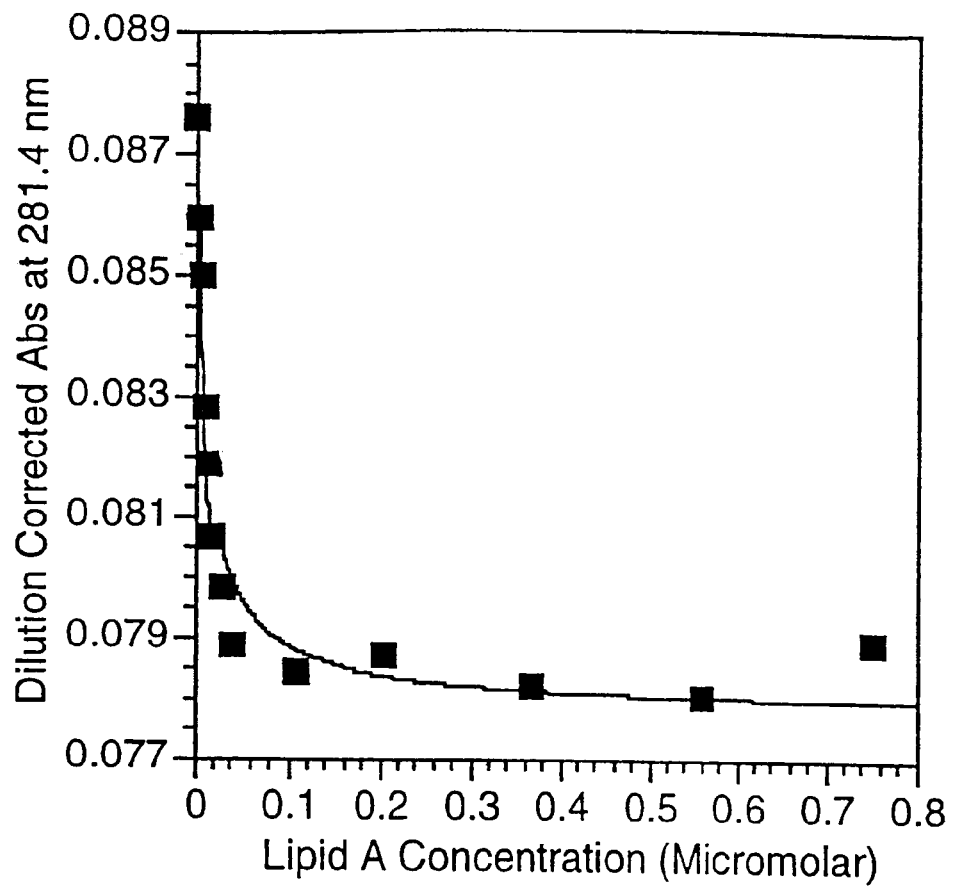
FIG. 3 is a graph illustrating the UV titration of the ter-cyclopentane tetra-tryptophanate derivative in PBS solution with lipid A.
Figure 4:
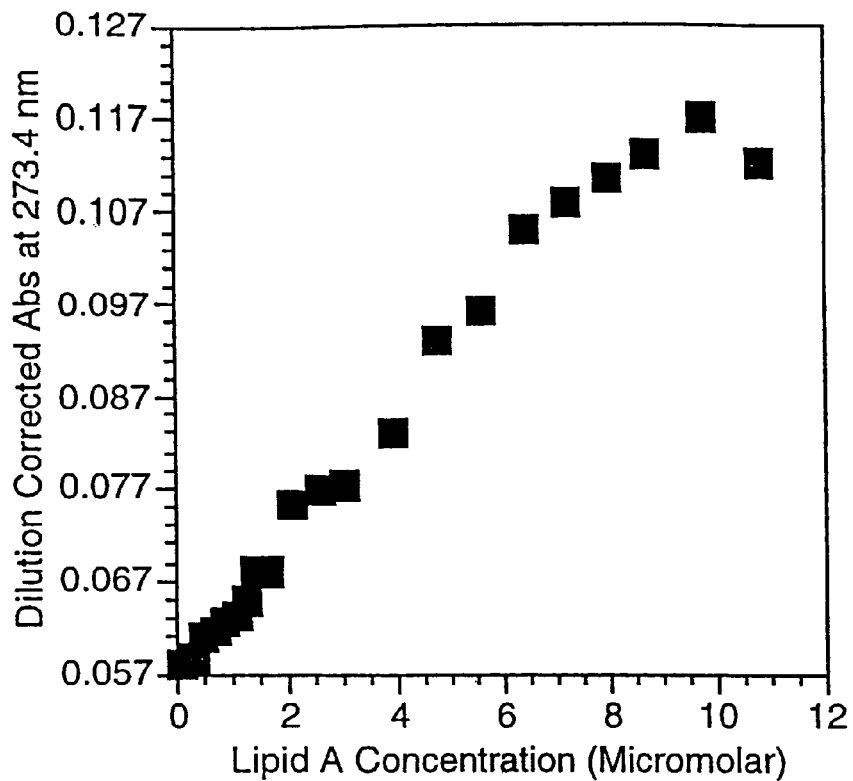
FIG. 4 is a graph illustrating the UV titration of the ter-cyclopentane tetra-glycinate derivative with lipid A in water.
Figure 5A:
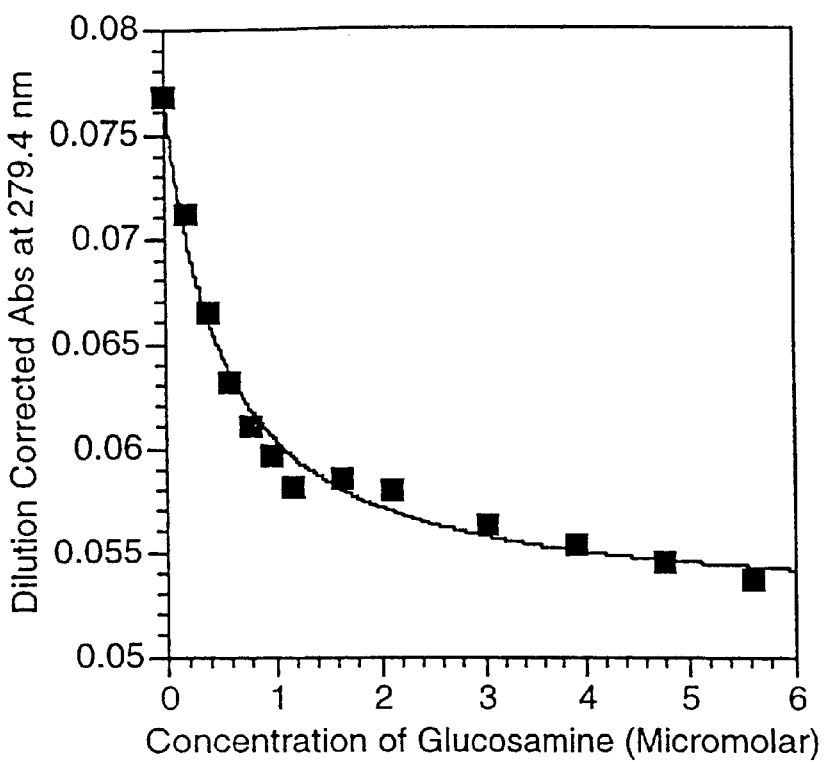
FIGS. 5A–B are graphs illustrating the UV titration of the ter-cyclopentane tetra-tryptophanate derivative with either glucosamine (5A) or glucose (5B) in water.
Figure 5B:
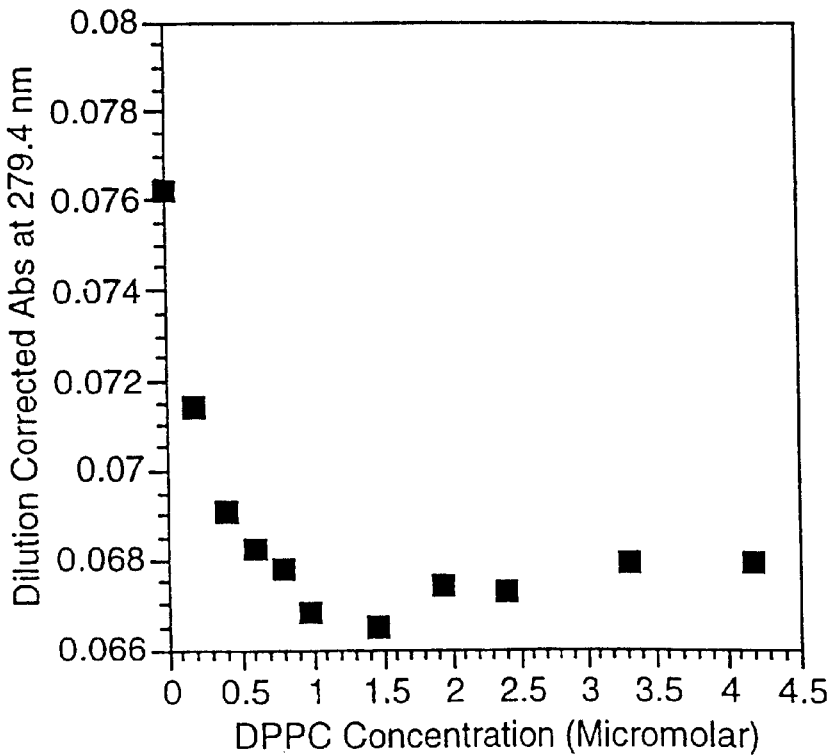

As shown in Table 2 below, 7.2 binds glucosamine with a dissociation constant, $K_D$, of 8.1 (PBS, pH 7.4) or 8.7 (water, pH 5.0) micromolar, while binding of 7.3 to glucosamine is approximately an order of magnitude stronger (350 nM in PBS, 446 nM in water, pH 5.0). Both of these affinities are notable in that they are two to three orders of magnitude stronger than values previously reported in the literature for other designed receptors for glucosamine (Schrader, *J. Org. Chem.* 63:264–272 (1998), which is hereby incorporated by reference). While 7.2 showed reasonable affinity for lipid A (FIG. 2), the 7 to 8 nM dissociation constant measured for 7.3 binding to lipid A (FIG. 3) is particularly striking, and is a full two orders of magnitude stronger than the reported polymyxin-lipid A interaction (David et al., *Biochim. Biophys. Acta* 1212:167–175 (1994), which is hereby incorporated by reference). Providing further indication of the importance of the amino acid side chains in the recognition process, a saturation point for binding of lipid A to 7.1 was not reached at concentrations below the critical micelle concentration (cmc) for lipid A (Hofer et al., *Chem. Phys. Lipids* 59:167–181 (1991); Aurell et al., *Biochem. Biophys. Res. Commun.* 253:119–123 (1998), which are hereby incorporated by reference), although changes in the UV absorbance clearly indicated the presence of some interaction (FIG. 4). The tremendous difference in the measured affinity of 7.3 for glucosamine over glucose in water at pH 5.0 is striking, and was somewhat unexpected (FIGS. 5A and 5B). Because 7.3 and glucosamine are both positively charged in aqueous solution, it was expected that formation of a 7.3-glucose complex would be favored over a 7.3-glucosamine complex.

TABLE 2

Binding Affinity of ter-Cyclopentane Tetra-amino Acid Derivatives

| Compound | Conditions | Affinity ($K_D$, nanomolar) | | |
|---|---|---|---|---|
| | | Glucose | Glucosamine | Lipid A |
| 7.1 (Gly) | PBS, pH 7.4 | — | no affinity | _3,000 |
| 7.2 (Phe) | PBS, pH 7.4 | — | 8,100 | 1,170 |
| 7.3 (Trp) | PBS, pH 7.4 | — | 350 | 8 |
| 7.1 (Gly) | water, pH 5.0 | — | no affinity | _3,000 |
| 7.2 (Phe) | water, pH 5.0 | — | 8,700 | ND |
| 7.3 (Trp) | water, pH 5.0 | 43,800 | 446 | 7 |
| Polymyxin B | water, pH 5.0 | — | — | 370* |
| $H_2N$-Trp-$OCH_3$ | PBS, pH 7.4 | — | — | _3,000 |

Figure 6:
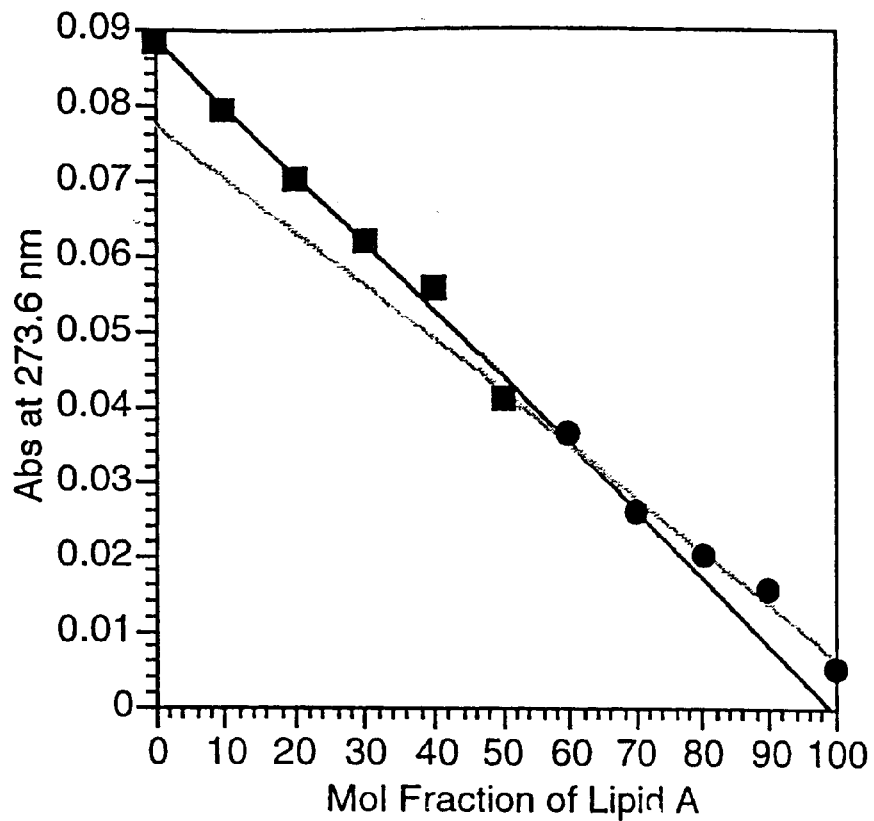
FIG. 6 is a Job's plot of the results of the UV titration of the ter-cyclopentane tetra-phenylanalinate derivative with lipid A in PBS.
Figure 7:
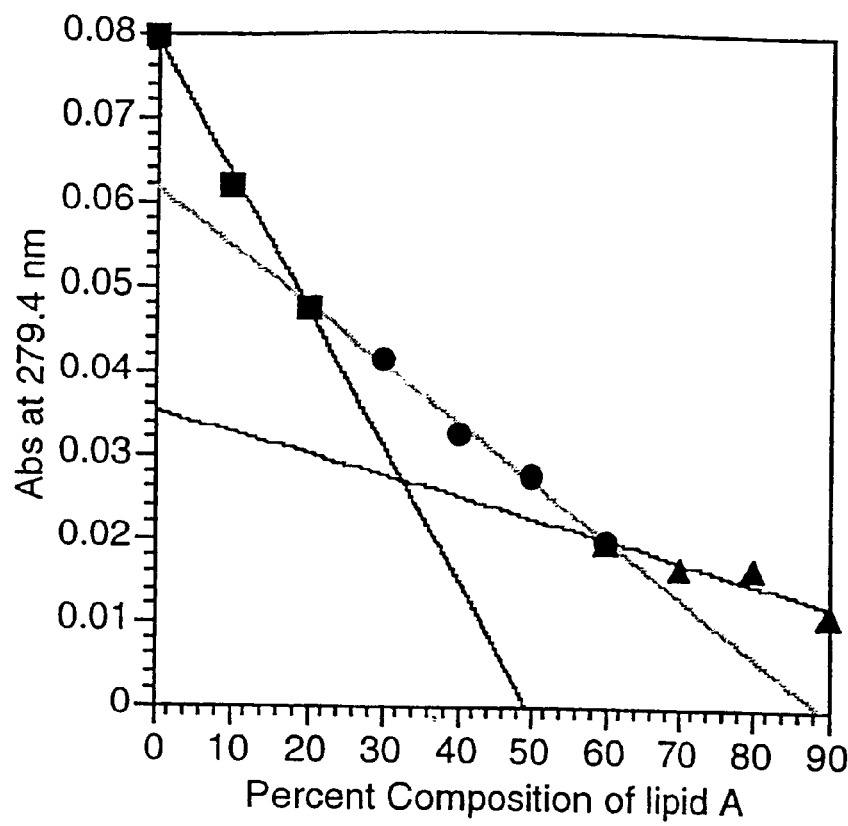
FIG. 7 is a Job's plot of the results of the UV titration of the ter-cyclopentane tetra-tryptophanate derivative with lipid A in water.
Figure 8:
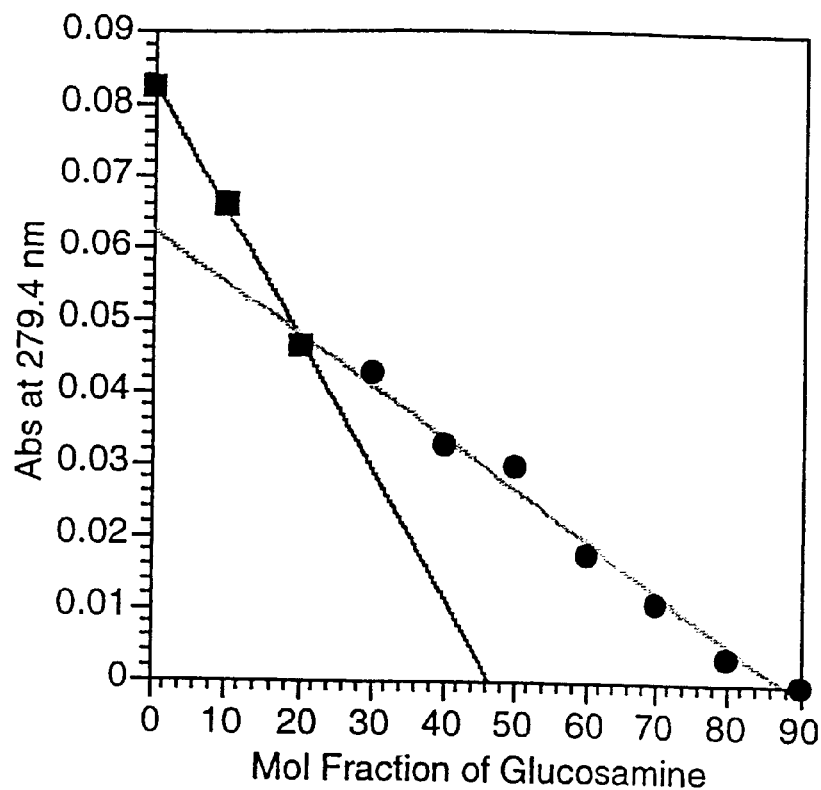
FIG. 8 is a Job's plot of the results of the UV titration of the ter-cyclopentane tetra-tryptophanate derivative with glucosamine in water.

*Reported in David et al., Biochim. Biophys. Acta 1212:167–175 (1994), which is hereby incorporated by reference The method of continuous variations (Job, *Compt. Rend.* 180:928 (1925); Blanda et al., *J. Org. Chem.* 54:4626 (1989), which are hereby incorporated by reference) was employed to further examine the binding of 7.2 and 7.3 to lipid A in aqueous solution. While titration curves suggested that 7.2 forms a 1:1 complex with lipid A and a 2:1 complex with glucosamine at saturation, Job's plot analysis of 7.2 binding to lipid A (FIG. 6) shows no clear inflection point, perhaps due to 7.2's relatively low extinction coefficient. However, two inflection points are clearly observable for 7.3 binding to lipid A (FIG. 7), the first indicating the formation of a 5:1 7.3:lipid A complex. A single inflection point was observed in the Job's plot of 7.3 with glucosamine (FIG. 8), corresponding to a 5:1 complex. To further clarify the mode of interaction between 7.1–7.3 and lipid A, dipalmitoyl phosphatidylcholine (DPPC) was titrated into solutions of 7.2 and 7.3. While some absorbance changes were observed in both cases, these were very weak (on the order of 10% overall), and did not display a standard saturation profile. An accurate assessment of the affinity, if any, of 7.2 or 7.3 for DPPC is complicated in part by the extraordinarily low critical micelle concentration of DPPC in water, 46 nM at 20° C. (Smith et al., *J. Mol. Biol.* 67:75–83 (1972), which is hereby incorporated by reference). This suggests that while there may be some interaction between 7.1–7.3 and the phospholipid tails of lipid A, it is likely nonspecific, and only weakly contributes to the overall affinity constant.

Figure 9:
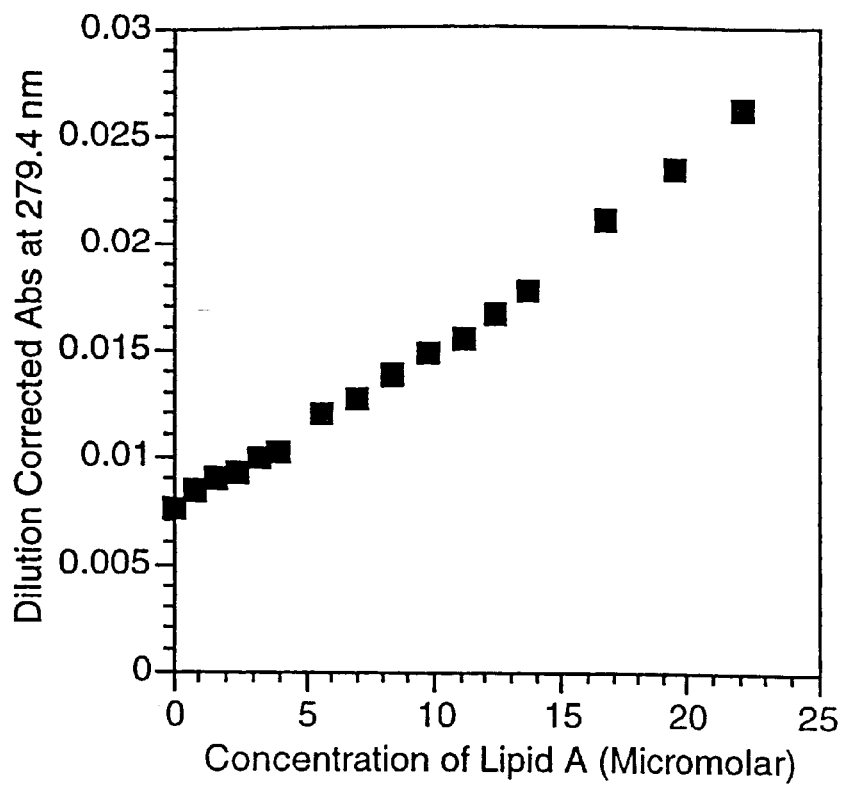
FIG. 9 is a graph illustrating the UV titration of tryptophan methyl-ester in water with lipid A.

To ensure that interactions were not simply due to the amino acid-derived functionality of 7.1–7.3, the binding of lipid A to the methyl ester of tryptophan was also examined. In aqueous solution, a linear increase in the tryptophan indole ring absorbance was observed on addition of increasing concentrations of lipid A (FIG. 9). However, this increase was not saturable at the concentrations tested (>20 micromolar in lipid A), indicating a strictly nonspecific interaction.

Thus, the highly substituted ter-cyclopentanes presented herein represent a new class of compounds which demonstrate unprecedented levels of affinity for simple sugars and lipid A in aqueous solution. For the phenylalanine-derivatized compound 7.2, titration curves suggest that binding to lipid A involves the formation of a 1:1 complex, while interaction with glucosamine appears to require the formation of a 2:1 complex. In contrast, the tryptophan-derivatized compound 7.3 appears to form a 5:1 complex with lipid A.

Example 9

Asymmetric Protection of Diol and Oxidative Cleavage of Norbornylene Fused Rings The diol 4.1 obtained from Example 4 was protected with the addition of silyl ether groups according to the scheme set forth below.

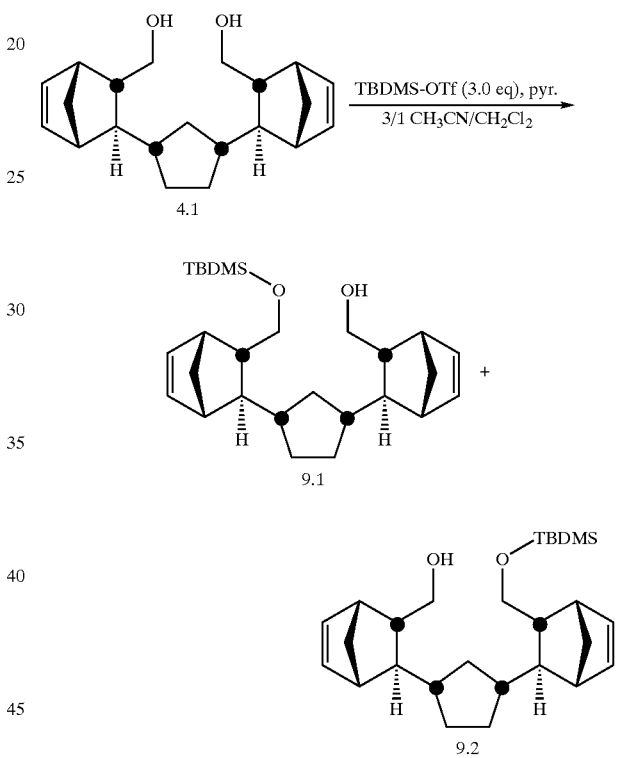

Treatment of the diol 4.1 with tert-butyldimethylsilyl trifluoromethanesulfate ("TBDMS-Otf") and pyridine resulted in only the mono-silyl-ether of 9.1 or 9.2, as determined by mass spectroscopy. It is believed that sterically hindered protecting groups may be best able to yield asymmetric protection of the diol 4.1.

Example 10

Unidirectional Synthesis of Diacid

As a measure of determining whether a ter-cycloalkanoid tetra-acid can be prepared according to a bi-directional procedure, the synthesis scheme was first conducted by preparing a diacid via a unidirectional synthesis.

The first step in the preparation of the diacid was the preparation of a β-ketophosphonate 10.3 intermediate according to the synthesis scheme below.

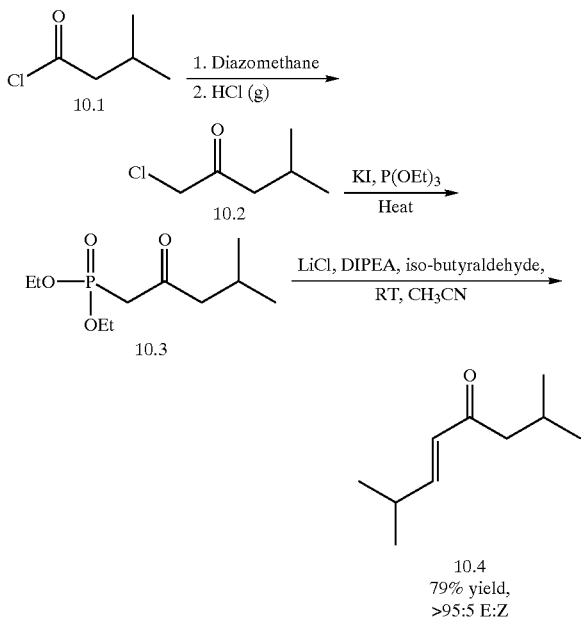

Following the procedure of Kitamura et al., (*J. Am. Chem. Soc.* 117:2931–2932 (1995), which is hereby incorporated by reference), the starting compound was iso-valeryl chloride (10.1), which was treated with diazomethane and then decomposed with HCl(g) to afford the α-chloroketone 10.2. Conversion of the chloride to the iodide with KI, followed by Arbuzov reaction with triethyl phosphite (P(OEt)$_3$), yielded β-phosphonate 10.3 in 55% yield from 10.1. This reaction sequence allowed for the synthesis of 20–30 g of 10.3, with the only difficulty being in the generation of large amounts of diazomethane.

In the next step, β-phosphonate 10.3 was converted to the ketone 10.4 using the conditions described by Blanchette et al. (*Tetrahedron Lett.* 25:2183–2186 (1984), which is hereby incorporated by reference). β-phosphonate 10.3 was treated with LiCl, N,N-diisopropylethylamine (DIPEA), and isobutyraldehyde in acetonitrile to afforded 10.4 in 79% yield and >95:5 E:Z.

Ketone 10.4 was used as starting material in a DA reaction according to the synthesis scheme below.

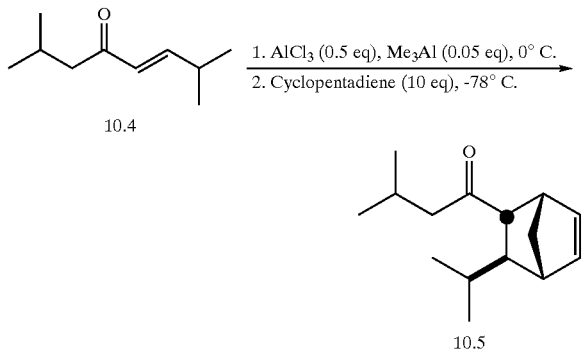

Dienophile 10.4 (3.07 g, 19.94 mmol) was dissolved with 25 mL of dry CH$_2$Cl$_2$ to afford a 0.8 M solution. The resulting solution was cooled to 0° C. for 10 min. Addition of Me$_3$Al (0.50 ml, 0.997 mmol, 2.0 M in hexanes) yielded slight gas evolution, which dissipated upon stirring at 0° C. for an additional 10 min. To the yellow solution, was added AlCl$_3$ (9.97 ml, 9.97 mmol, 1.0 M in CH$_3$NO$_2$) and the reaction was stirred an additional 5 min at 0° C. The reaction was cooled to −78° C. for 10 min, to which, was added cyclopentadiene (13.16 g, 199.4 mmol, 5.0 M in CH$_2$Cl$_2$). Upon addition of the diene, the reaction formed a thick white precipitate. The reaction was allowed to stir at −78° C. for 2 hr. After quenching the DA reaction with pyridine (10 ml, 125 mmol), the reaction was quickly warmed to RT. The resulting thick white slurry was filtered through silica (250 ml), and washed with Et$_2$O (4×60 ml). The organics were reduced in vacuo. Azeotropic removal of the pyridine and CH$_3$NO$_2$ was affected by treatment with heptane (4×50 ml) affording a yellow residue. Purification via flash chromatography (silica, 95:5, hexanes:Et$_2$O) afforded 10.5 as a yellow oil (3.55 g, 81% yield). NMR and mass-spectometry analyses confirmed the identity of the DA adduct 10.5.

The DA adduct 10.5 was then converted to diacid 10.6 according the synthesis scheme below.

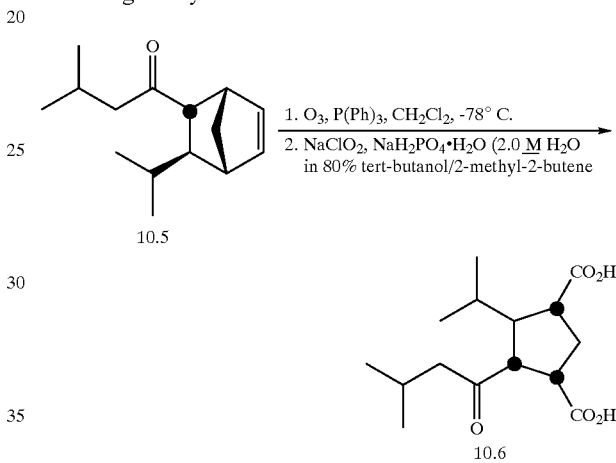

Diels-Alder adduct 10.5 (3.03 g, 13.77 mmol) was dissolved into CH$_2$Cl$_2$ (125 ml) and cooled to −78° C. for 30 min (see Lindgren et al., *Acta. Chem. Scand.* 27:888–890 (1973); Carreira et al., *J. Am. Chem. Soc.* 117:8106–8125 (1995), which are hereby incorporated by reference). Ozone (O$_3$) was bubbled into the solution until the reaction attained a blue color (20 min), then continued O$_3$ for an additional 30 min. The ozone generator was turned off, and bubbled O$_2$ through the system to remove excess O$_3$. After the blue color had dissipated, the reaction was warmed to 0° C. for 15 min. The reaction was quenched portionwise with triphenylphosphine (PPh$_3$, 4.35 g, 16.35 mmol). After addition of PPh$_3$ was complete, the reaction stirred for 1 hr at 0° C., or until starch paper revealed that all of the peroxides had been consumed. Reaction contents were reduced in vacuo and carried on crude. The crude dialdehyde was dissolved into 70 ml of an 80:20 tert-butanol:2-methyl-2-butene solution at RT. NaClO$_2$ (22.6 g, 250.6 mmol), and NaH$_2$PO$_4$.H$_2$O (26.60, 192.7 mmol) were dissolved into 225 ml of H$_2$O. The resulting solution was added via an additional funnel to the aldehyde solution over 1 hr. The reaction was stirred for 18 hr at RT. Upon addition of the NaClO$_2$ solution, the reaction became bright yellow, and eventually became opaque. The reaction contents were bacified with saturated aqueous (sat. aq.) Na$_2$CO$_3$, and extracted 5×100 ml of Et$_2$O. The aqueous layer was carefully acidified to a pH=3, with an aqueous buffered solution of NaH$_2$PO$_4$.H$_2$O/concentrated HCl (pH=2–3). The resulting aqueous was extracted sequentially with 6×100 ml of EtOAc, and 5×100 ml of CH$_2$Cl$_2$.

The combined EtOAc and $CH_2Cl_2$ washes were dried over $Na_2SO_4$, filtered and reduced in vacuo to afford a white solid. Recrystallization of the crude diacid with benzene afforded 5.35 as a white solid (2.94 g, 75% yield).

Example 11

Asymmetric Introduction of Functional Group Onto Diacid

Using the diacid 10.6 prepared according to Example 10, an intermediate anhydride is formed and opened via a nucleophile according to the reaction scheme below.

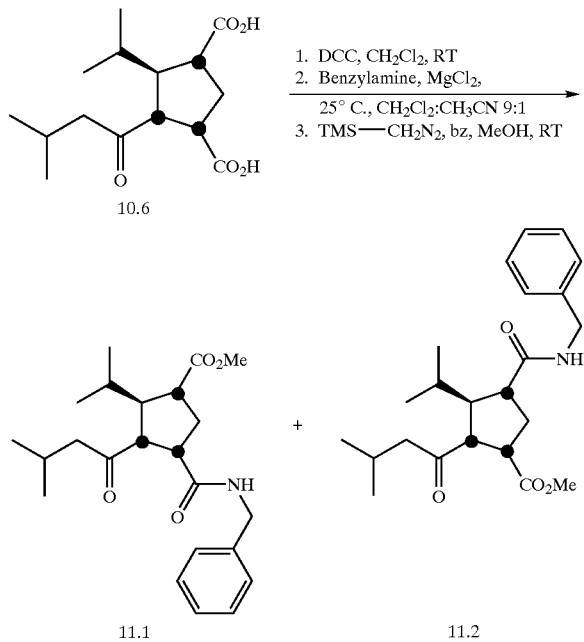

The diacid 10.6 (114.3 mg, 0.403 mmol) was dissolved into 0.7 M $CH_2Cl_2$ at room temperature. To the colorless, homogeneous reaction was added DCC (82.9 mg, 0.402 mmol) at room temperature (see Yamazaki et al., Chem. Pharm. Bull. 35:3453–3459 (1987), which is hereby incorporated by reference). Upon addition of DCC to the reaction, an immediate white precipitate formed. The reaction was allowed to stir for 5 hr at room temperature, then filtered through Celite. The Celite pad was washed with $CH_2Cl_2$ (5×2 ml). The combined organics were reduced in vacuo to afford a white solid, that was used without further purification. The crude anhydride was dissolved into a 0.3 M solution of $CH_2Cl_2:CH_3CN$ 9:1 at RT. $MgCl_2$ (45.93 mg, 0.48 mmol) was added to the solution and stirred for 10 min at room temperature. Upon dropwise addition of the amine to the solution, the reaction went from opaque to white in color. The reaction stirred for 18 hr at RT. The reaction was quenched with by acidifing to a pH=1, with 10% HCl solution. Extraction with $CH_2Cl_2$, followed by drying over $Na_2SO_4$, filtering and reduction of the volume in vacuo afforded a yellow residue. The residue was dissolved into a 0.11 M solution of 28% methanolic benzene at room temperature. Dropwise addition of TMS-$CH_2N_2$ resulted in vigorous gas evolution. After stirring for 2 hr, the reaction was filtered through silica, eluting with EtOAc, and reaction in vacuo afforded a yellow oil. Crude $^1H$ NMR of the reaction mixture revealed that the opening of the anhydride occurred with 5.3/1 selectivity 11.2:11.1. The reaction was purified via flash chromatography (silica, 75:25, hexanes::ethyl acetate) which afforded 11.2 and 11.1 in a combined yield of 99 mg, and in 64% yield.

Treatment of the reaction intermediate anhydride with benzylamine was performed under a variety of conditions shown in Table 3 below, and subsequent esterification of the resulting acids with TMS-diazomethane afforded esters 11.2 and 11.3. The integration of the regioisomeric methyl resonances was used to determine the selectivity of the reaction. As shown in Table 3 below, the iso-valeryl group of the ketone was sterically demanding enough to attain some regioselectivity in the absence of a Lewis acid, which afforded 11.3 and 11.2 in a 1.8:1 ratio (Entry 1). Interestingly, when LiCl was employed as a Lewis acid catalyst, at −20° C. it afforded selectivities comparable to $MgCl_2$ at 25° C. (Entries 6 vs. 7), while the selectivity of the $MgCl_2$-promoted reaction is actually lower at reduced temperatures. Without being bound by theory, it is believed that the selectivity demonstrated with benzylamine nucleophilic opening of 11.1 with both $MgCl_2$ at 25° C., and with LiCl at −20° C. is the result of the vibrational energy of the anhydride under the specified reaction temperatures. At lower temperatures (−20° C.), the system possesses less vibrational energy; therefore, the bicyclic system is much more compact than at higher temperatures, allowing a chelate formed by the smaller lithium cation to be more favored. However, at higher temperatures, the system possesses the vibrational energy to allow the bicyclic system to stretch such that the ketone carbonyl and the anhydride carbonyl are far enough apart to allow for chelation by the larger magnesium cation.

TABLE 3

Asymmetric Nucleophilic Opening of Anhydride

| Entry | Temp (° C.) | Lewis Acid (eq) | Regioselectivity (5.42/5.41) | Yield (%) |
|---|---|---|---|---|
| 1 | 25 | None | 1.8/1 | 40–60 |
| 2 | 25 | LiCl | 3.4/1 | 72 |
| 3 | 4 | LiCl | 4.5/1 | 65 |
| 4 | −20 | LiCl | 5.0/1 | 59 |
| 5 | 25 | $MgCl_2$ | 5.3/1 | 64 |
| 6 | 4 | $MgCl_2$ | 4.5/1 | 37 |
| 7 | −20 | $MgCl_2$ | 3.5/1 | 42 |
| 8 | 4 | $MgCl_2$ (2.5) | 2/1 | 56 |
| 9 | 4 | $(Cp)_2TiCl_2$ | 2.6/1 | 29 |
| 10 | 25 | $Sc(OTf)_3$ | 1.5/1 | 21 |

Example 12

Unidirectional Synthesis of Asymmetric Compound 11.2 Via Lactone Intermediate Starting with intermediate 10.5 prepared in Example 10, the keto group was reduced to an alcohol, yielding diastereomeric alcohols 12.1 and 12.2 as noted in the synthesis scheme below, using the various reaction conditions set forth in Table 4 below.

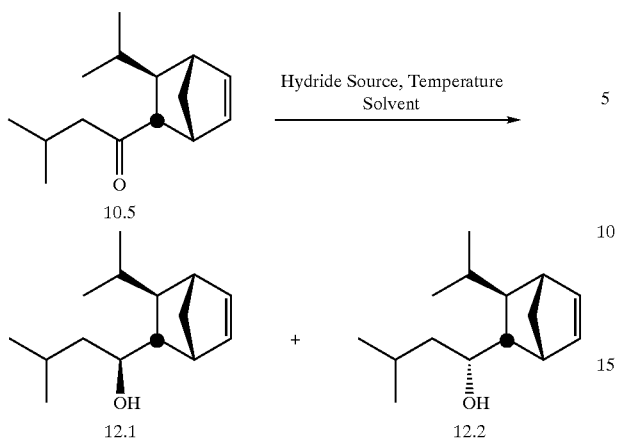

By way of example, ketone 10.5 (75.7 mg, 0.34 mmol) was dissolved into 0.5 M THF at RT. After cooling the solution to −78° C. for 15 min, L-selectride (0.71 ml, 0.71 mmol, 1.0 M solution in THF) was added via syringe. After stirring at 1 hr at −78° C., TLC analysis of the reaction showed only SM (starting material). The reaction was warmed to 0° C. over 4 hr, TLC showed complete consumption of SM. Reaction was quenched sequentially with 0.7 ml of 15% NaOH, 0.7 ml of 30% $H_2O_2$. The reaction mixture was extracted with $CH_2Cl_2$ (3×5 ml). The organic extracts were pooled, dried over $Na_2SO_4$, filtered and reduced in vacuo to give an oil that recrystallized upon standing. The residue was purified via flash chromatography (silica, 88:12 hexanes:$Et_2O$) to give 55 mg of both 12.1 and 12.2 in a 2.4:1 ratio of 12.1:12.2.

TABLE 4

Hydride Reduction of Keto Group

| Entry | Hydride Source | Solvent | Temperature (° C.) | Yield (%) | Selectivity (5.44:5.45) |
|---|---|---|---|---|---|
| 1 | LAH | THF | 0 | 63 | 1.8:1 |
| 2 | LAH | THF | −78 | 76 | 1.4:1 |
| 3 | DIBAL-H | THF | 0 | 70 | 2.2:1 |
| 4 | L-selectride | THF | −78 to 0 (4 hr) | 72 | 2.4:1 |
| 5 | L-selectride | THF | −78 to 0 (15 min) | 80 | 1:1.6 |
| 6 | L-selectride | THF | 25 | 76 | 1:2.4 |
| 7 | L-selectride | $Et_2O$ | 25 | 32 | 1:3 |

The diastereoselectivity of the reaction, albeit modest in all cases, seemed to be independent of the size of the hydride source (Entry 1 vs. Entry 4). However, the temperature at which the reduction was performed seemed to dramatically affect which diastereomer forms (Entry 4 vs. Entry 6).

Initially, the assignments of 12.1 and 12.2 were based solely on analysis of the $^1$H NMR, and of the resulting TLC of the reaction. TLC indicated that one of the diastereomeric alcohols possessed a much higher $R_f$ (retention factor) than the other. That compound also possessed a $^1$H NMR spectrum that showed the methine protons of the [2.2.1] bridgehead were in very similar magnetic environments. Finally, this particular alcohol was isolated as a liquid. All of these factors indicated that et-diastereomer 12.2 was the alcohol in question. The conformation of the alcohol in 12.2 would be expected to shield the hydroxyl group from silica, yielding a higher $R_f$, and simultaneously generating a pseudo-symmetric bicyclic compound. We were able to confirm these assertions with the solution of a single X-ray crystal of 12.1, the diastereomer that was isolated as a solid. The crystal structure not only determined which diastereomer was a solid, but proved that the Diels-Alder reaction to which generated 10.5 was endo-selective. Finally, the X-ray crystal structure of 12.1 confirmed the stereoselectivity of the Homer-Wadsworth-Emmons reaction, which provided 10.4.

After chromatographic separation of 12.1 and 12.2, each diastereomer was subjected separately to the following reaction sequence in order to assure that the chemistry was applicable with each molecule. At this point, it was desirable to retain the oxidation state of the carboxylic acid, and only modify the carbonyl such that it was more resistant to nucleophilic attack. This would be accomplished by conversion of the acid moiety to the tert-butyl ester according to the following scheme.

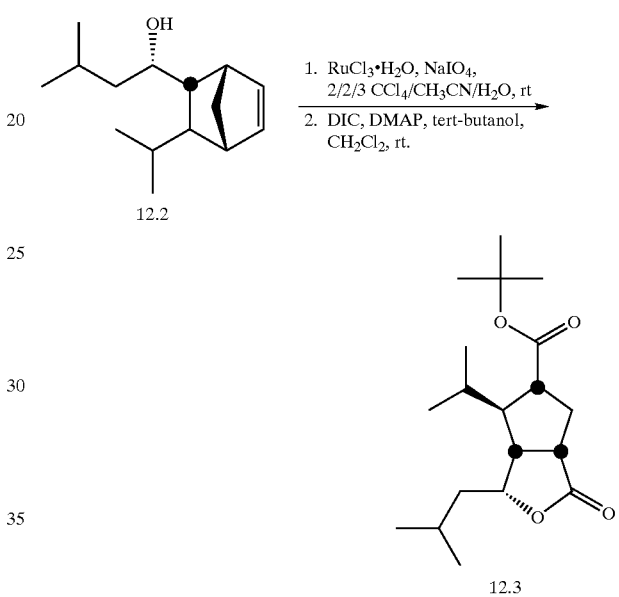

Alcohol 12.2 (1.00 g, 4.50 mmol) was dissolved into a 0.11 M solution of 2/2/3 $CH_3CN/CCl_4/H_2O$ (Carlsen et al., J. Org. Chem. 46:3936–3938 (1981), which is hereby incorporated by reference) at room temperature. Addition of $NaIO_4$ (5.76 g, 27.0 mmol), and $RuCl_3.H_2O$ (18 mg, 0.09 mmol) caused formation of a white precipitate. The reaction was allowed to stir for 8 hr at room temperature. The reaction was quenched sequentially with water (2 ml) and aq 10% HCl solution until the pH=1. The aqueous layer was extracted with $CH_2Cl_2$ (4×15 ml), and filtered through Celite. The filtrate was reduced in vauco, to afford a purple solid, which was used without further purification.

Presence of the lactone was confirmed by IR spectroscopy, which displayed a C═O stretch of 1768 cm$^{-1}$, indicative of a 5-membered lactone (Pavia et al., Introduction to Spectroscopy: A Guide for Students of Organic Chemistry, Harcourt Brace Jovanovich College Publishers, Fort Worth, Tex., p. 48 (1979), which is hereby incorporated by reference).

The crude acid was dissolved into 0.6 M $CH_2Cl_2$ at 0° C. for 10 min. To the purple solution, sequential addition of tert-butanol (0.50 ml, 6.75 mmol), DMAP (0.11 g, 0.90 mmol) (Dhaon et al., J. Org. Chem. 47:1962–1965 (1982), which is hereby incorporated by reference), and DIC (0.99 ml, 6.3 mmol) resulted in formation of a precipitate. After the reaction stirred at room temperature for 24 hr, the reaction was quenched with water (2 ml) and 10% aq HCl solution until the pH=1. Extraction of the reaction with CH$_2$Cl$_2$, followed by drying the organics over Na$_2$SO$_4$, filtering and reduction of the solvent in vacuo yielded a purple oil. Purification of the reaction via flash chromatography (silica, 75:25 hexanes:ethyl acetate) afforded a 12.3 as a white solid (0.87 g, 60% yield).

The t-butyl protected compound 12.3 was then treated according to the synthesis scheme below.

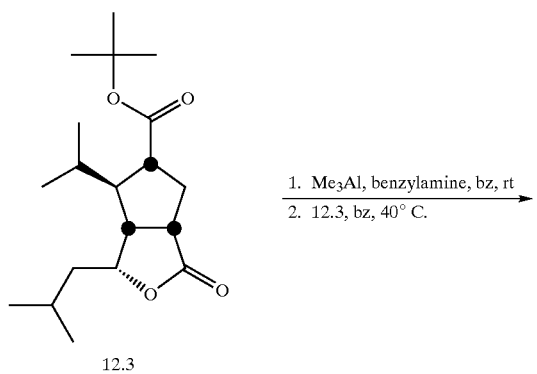

Benzyl amine (0.22 ml, 2.0 mmol) was dissolved into 5.0 ml of benzene at room temperature. Me$_3$Al (1.0 ml, 2.0 mmol, 2.0 M in hexanes) was added dropwise, via a syringe, to the benzene solution. The reaction was stirred at vortex speeds for 15 min. Concurrently, 12.3 (40.0 mg, 0.13 mmol) was dissolved into 0.1 ml of bz at room temperature. The aluminate of benzyl amine (0.79 ml, 0.32 mmol, 0.4 M in bz) was added dropwise, via syringe, to the benzene solution of 12.3. The reaction was immediately warmed to 50° C., stirred at this temperature for 5 hr. The reaction was cooled to room temperature, and immediately quenched with 10% aq. solution of HCl until the pH=1. Extraction of the resulting aqueous solution with CH$_2$Cl$_2$ (5×5 ml), drying the organics over Na$_2$SO$_4$, subsequent filtering, and reduction of the solvent in vacuo afforded an off-white solid. Purification of the solid via flash chromatography (silica, 75:25 hexanes:ethyl acetate) yielded 12.6 as a white solid (37 mg, 68% yield).

Oxidation of the resulting alcohol 12.6 proceeded according to the Dess-Martin Periodinane (Dess et al., *J. Am. Chem. Soc.* 113:7277 (1991), which is hereby incorporated by reference) scheme below.

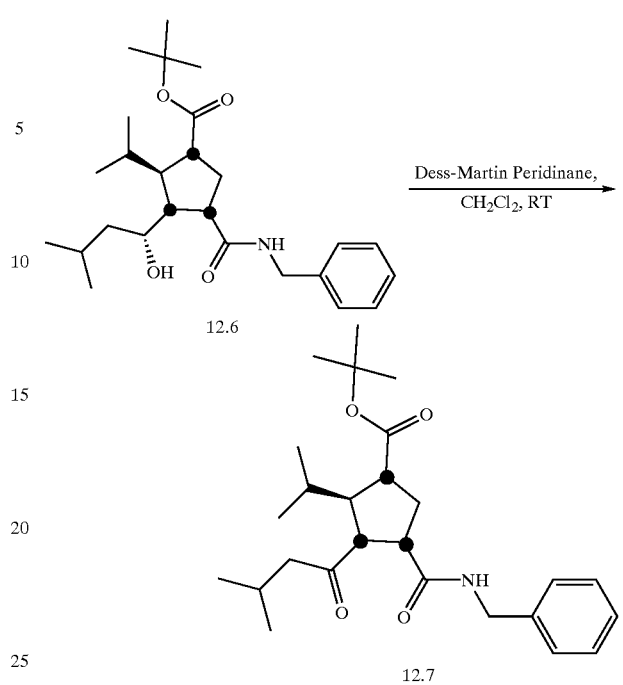

Dess-Martin Periodinane Reagent (42 mg, 0.10 mmol) was slurried into 0.3 ml of CH$_2$Cl$_2$ at room temperature. To this solution, alcohol 12.6 (22.5 mg, 0.05 mmol) in 0.2 ml of CH$_2$Cl$_2$ was added at room temperature. The reaction immediately cleared upon addition of 12.6. After the reaction stirred for 1 hr, TLC showed consumption of SM. The reaction was quenched with sat aq. Na$_2$CO$_3$ until pH=10. The aqueous was extracted with CH$_2$Cl$_2$ (5×2 ml). The organics were combined, dried over Na$_2$SO$_4$, filtered, and reduction of solvent in vacuo afforded a white solid. Purification of the resulting solid via flash chromatography (silica, 80:20 hexanes:ethyl acetate) yielded 12.7 as a white solid (12 mg, 54% yield).

Removal of the t-butyl protecting group can be achieved according to the synthesis scheme below.

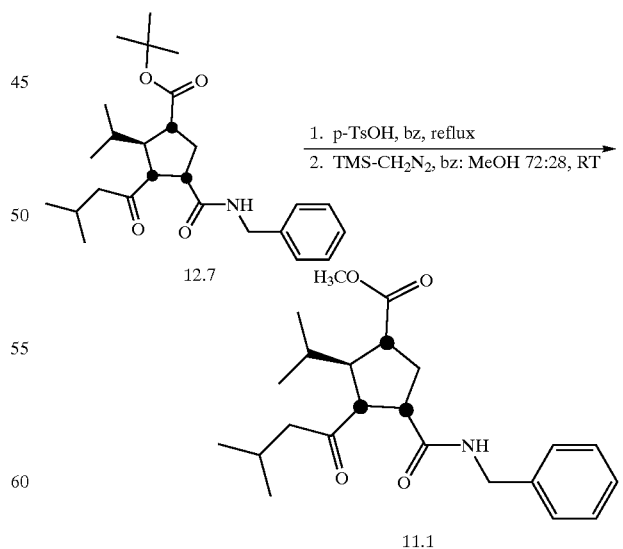

Ester 12.7 (76 mg, 0.18 mmol) was dissolved into 2.0 ml of bz at RT, added p-TsOH.H$_2$O (3.36 mg, 0.018 mmol) and heated reaction contents to relfux. After heating at reflux for 2 hr, the reaction had consumed SM by TLC. The reaction was allowed to cool to room temperature, contents were reduced in vacuo, and used without further purification. The crude acid was dissolved into 0.11 M solution of 28% methanolic benzene at room temperature. TMS-CH$_2$N$_2$ (0.35 ml, 0.71 mmol) was added dropwise via a syringe, resulting in vigorous gas evolution. After stirring for 2 hr at room temperature, the reaction contents were reduced in vacuo. Purification of the resulting residue via flash chromatography (silica, 75:25 hexanes:ethyl acetate) afforded a colorless oil (55 mg, 81% yield). The spectral characteristics matched the minor product isolated from the nucleophilic opening anhydride 11.1.

room temperature for 10 min, a thick orange-white precipitate formed. After 12 hr at room temperature, the reaction was quenched with 20 ml of water, and the resulting layers were separated. The aqueous was extracted with ether (3×20 ml). The organic layers were combined, dried over Na$_2$SO$_4$, filtered, and reduced in vacuo to afford a thick red-orange oil. Purification of crude ketone via flash chromatography (silica, 95:5 hexanes:ethyl acetate) afforded 13.3 as a yellow oil (2.91 g, 71% yield, E,E:E,Z 63:1).

The bis-dienophilic ketone 13.3 was treated as follows.

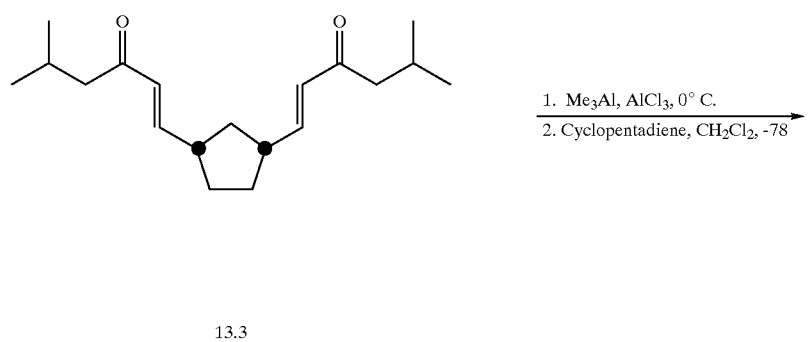

Example 13

Bidirectional Synthesis of Asymmetric Oligocycloalkanoid Compound Via Nucleophilic Attack of Anhydride Intermediate Synthesis of the anhydride intermediate was performed as described in the following reaction schemes. Using nor-bornylene as a starting material, oxidative cleavage with ozone (O$_3$) and triphenyl phosphine (PPh$_3$) was performed to yield dialadehyde 13.1.

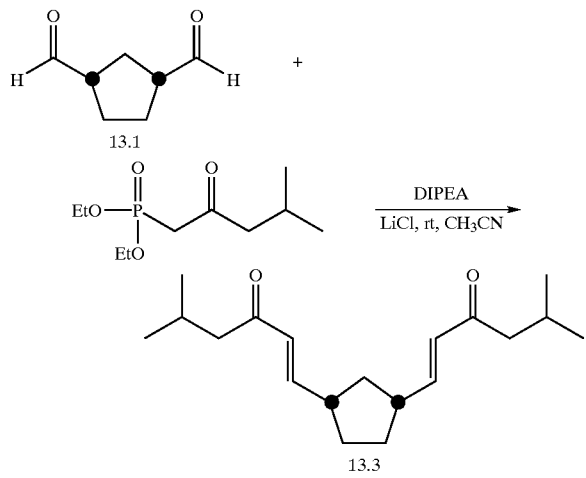

LiCl (1.34 g, 31.6 mmol) was dissolved into 18 ml of CH3CN at RT. Sequential addition of 13.2 (6.56 g, 31.6 mmol), DIPEA (4.69 ml, 28.8 mmol), followed by and aldehyde 13.1 (1.82 g, 14.4 mmol) in 6 ml of THF afforded a yellow, homogeneous reaction mixture. After stirring at The dienophilic ketone 13.3 (2.9 g, 10.0 mmol) was dissolved into 0.5 M CH$_2$Cl$_2$ at 0° C. for 10 min. To which, Me$_3$Al (0.25 ml, 0.50 mmol) was added dropwise resulting slight gas evolution. After stirring for 10 min at 0° C., AlCl$_3$ (5.0 ml, 5.0 mmol, 1.0 M in CH$_3$NO$_2$) was added over 5 min to the yellow colored reaction. After stirring at 0° C. for an additional 10 min, the reaction was cooled to −78° C. for 10 min. Cyclopentadiene (8.5 ml, 100 mmol, in 20 ml of CH$_2$CL$_2$) was added via an addition funnel over 15 min. During the addition of the diene, a white precipitate formed. After stirring for 3 hr at −78° C., the reaction was quenched with pyridine (20 ml), and allowed to quickly warm to room temperature. The reaction was filtered through silica, eluting with ether (3×30 ml). The eluent was reduced in vacuo, and the resulting residue was azeotroped with heptane (4×30 ml). Purification of the resulting tan oil via flash chromatography (silica, 95:5 to 70:30 hexanes:ether) afforded 13.4 was a white solid (3.64 g, 82% yield, endo,endo:endo,exo= 94:6).

The higher reactivity of the ketone substrates in 13.3 not only allowed the DA reaction to occur at low temperatures, but also caused the reaction to decompose the unused diene, allowing for trivial purification of the reaction. The reaction volume was reduced in vacuo and placed on a lyophilizer for rigorous drying, affording a crystalline solid that was suitable for single X-ray crystallographic analysis. The crystal structure of 13.4 was crucial in proving that the major regioisomer of olefination was E, E, and simultaneously proved that the major diastereomeric cycloadduct from the DA reaction was endo, endo.

The DA adduct 13.4 was oxidized, as indicated the reaction scheme below, by ozonolysis with a reductive work-up of PPh$_3$ to yield a tetra-aldehyde, which was oxidized to the tetra-acid 13.5 under Lindgren conditions in 62% overall yield from 13.4. Treatment of the tetra-acid 13.5 with DCC in CH$_3$CN afforded bi-directional anhydride 13.5.

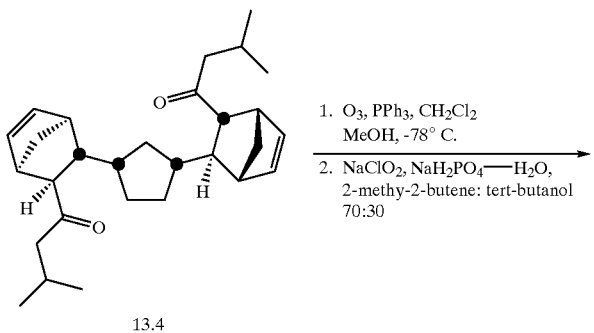

13.4

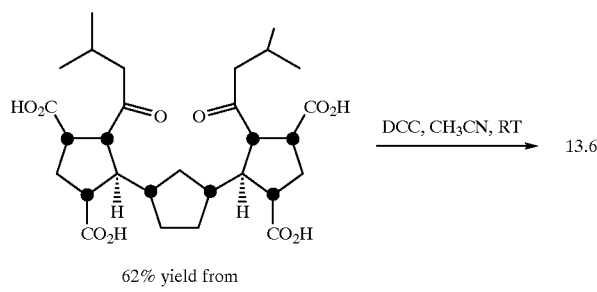

62% yield from
13.5

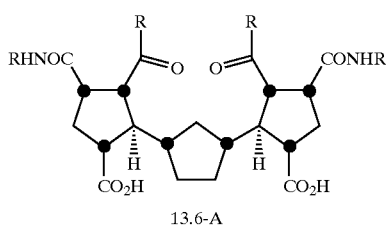

13.6-A

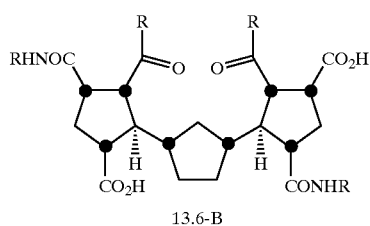

13.6-B

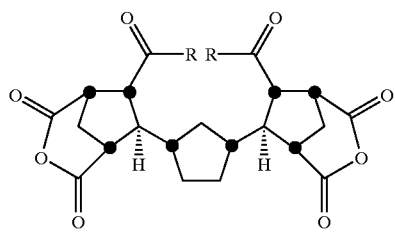

13.6

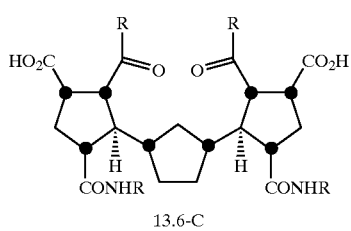

13.6-C

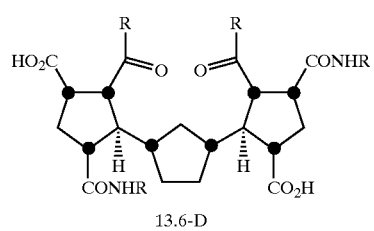

13.6-D

Under a variety of reaction conditions, nucleophilic opening of 13.5 yielded mixtures of compounds 13.6A-D that were difficult to separate and isolate.

Example 14

Proposed Bidirectional Synthesis of Asymmetric Oligocycloalkanoid Compound Via Protective Silylation Starting with an asymmetric Diels-Alder reaction of the known chiral dienophile 14.1 and cyclopentadiene in the presence of Et$_2$AlCl would give the known cycloadduct 14.2 (Evans et al., *J. Am. Chem. Soc.* 110:1238–1256 (1988), which is hereby incorporated by reference). LAH mediated reduction of the ester in 14.2 and subsequent protection with tert-butyldiphenylsilyl chloride ("TBDPS-Cl") and imidazole in CH$_2$Cl$_2$ would afford 14.3 (Hanessian et al., *Can. J. Chem.* 53:2975–2977 (1975), which is hereby incorporated by reference). The choice of the bulky-ultraviolet active protecting group was a non-trivial choice. An UV-active moiety is a useful aid in following reaction progress in subsequent chemical steps. Also, the silylether can be cleaved using conditions that would not cleave amides or esters present in the molecule.

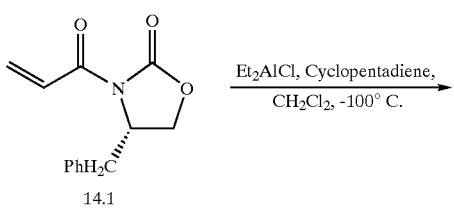

14.1

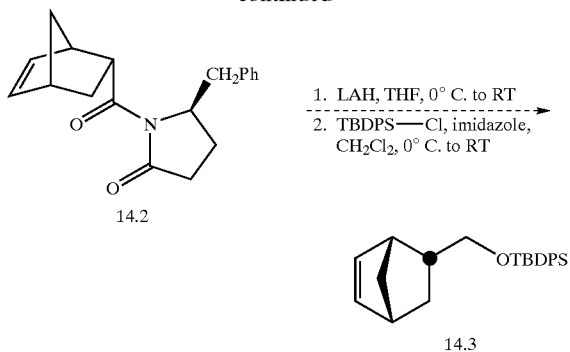

The resulting silyl-ether protected norbornylene 14.3 is then used as the starting material for preparation of an oligocycloalkanoid compound according to the synthesis scheme below.

butoxide and P-ester phosphonate 14.5 would give the bis-dienophilic ester 14.6. Submission of 14.6 to DA reaction conditions, Me₃Al and AlCl₃ with cyclopentadiene, would afford 14.7. Reduction of 14.7 with LAH followed by methylation (Johnstone et al., *Tetrahedron* 35:2169–2173 (1979), which is hereby incorporated by reference) of the resulting diol would afford 14.8. Oxidation of 14.8 with RuCl₃.H₂O and NaIO₄ would give the acid, which upon treatment with DCC in CH₂Cl₂ would give anhydride 14.9. Bi-directional anhydride 14.9 would be treated with a variety of Lewis acids and nucleophiles in an attempt to determine the regioselectivity associated with opening anhydride 14.9.

The silyl-ether moiety would give one an UV-signature to look for during standard TLC analysis of reaction progress. Therefore, this could also enable desymmetrization based on nucleophilic opening of substituted anhydrides.

Although the invention has been described in detail for the purpose of illustration, it is understood that such detail is solely for that purpose, and variations can be made therein

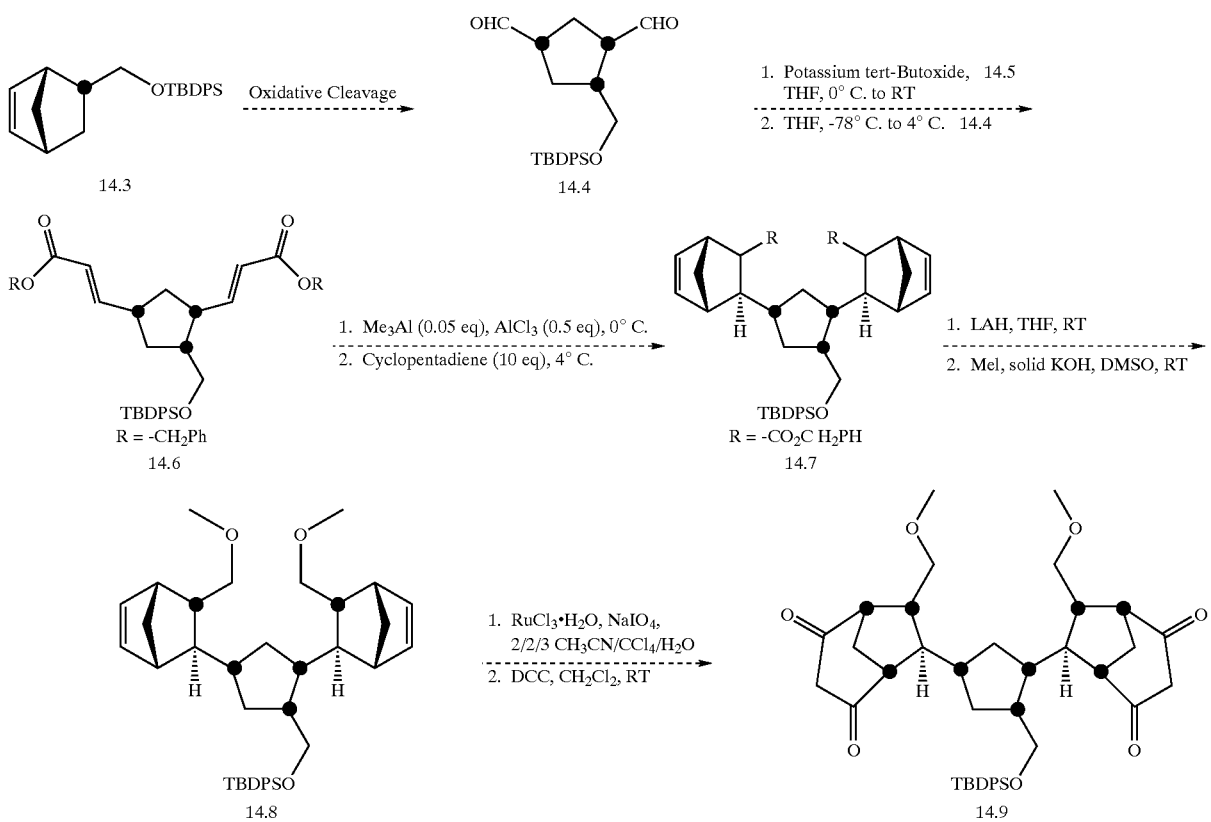

Reagents:

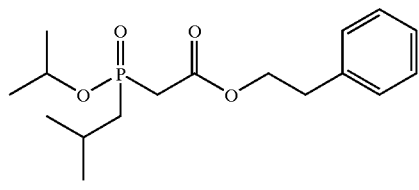

The silyl ether 14.3 would be oxidatively cleaved, either with O₃ or dihydroxylation and subsequent NaIO₄ cleavage, to the di-aldehyde 14.4. Olefination using potassium tert-butoxide and P-ester phosphonate 14.5 would give the by those skilled in the art without departing from the spirit and scope of the invention which is defined by the following claims.

What is claimed is:

1. An oligocycloalkanoid compound comprising formula (I)

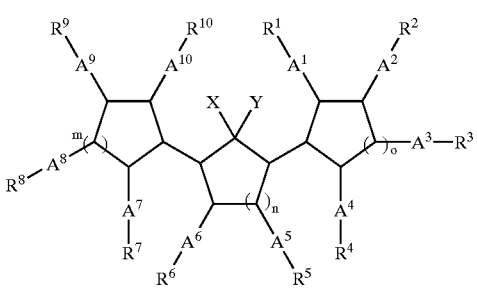

wherein m, n, and o are independently an integer from 0 to 2;

$A^1$ through $A^{10}$ are independently a direct link, alkylene, alkylene-O—, carbonyl, oxygen, or sulfur;

X and Y are independently hydrogen, hydroxy, alkyl, or in combination an electrophilic group; and $R^1$ through $R^{10}$ are independently hydrogen, hydroxy, alkyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoalkylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, or polypeptide, with at least one of $R^1$ through $R^4$ and at least one of $R^7$ through $R^{10}$ being other than hydrogen or hydroxy;

wherein when $A^1$, $A^3$, $A^4$, $A^7$, $A^9$, and $A^{10}$ are carbonyl, $R^1$, $R^3$, $R^4$, $R^7$, $R^9$, and $R^{10}$ are not simultaneously alkoxy, phenylethoxy, or 3-phenylpropoxy, and wherein $R^3$ and $R^8$ are not hydroxy when $A^3$ and $A^8$ are alkylene.

2. The compound according to claim 1, wherein m and o are 1;

$A^3$, $A^5$, $A^6$, and $A^8$ are direct links and $A^1$, $A^2$, $A^4$, $A^7$, $A^9$, and $A^{10}$ are carbonyl; and $R^3$, $R^5$, $R^6$, and $R^8$ are hydrogen.

3. The compound according to claim 2, wherein $R^1$, $R^2$, $R^4$, $R^7$, $R^9$, and $R^{10}$ are independently hydroxy, alkyl, aryl, aryloxy, amino, alkylamino, or arylalkylamino.

4. The compound according to claim 1, wherein m and o are 1;

$A^3$, $A^5$, $A^6$, and $A^8$ are direct links and $A^1$, $A^2$, $A^4$, $A^7$, $A^9$, and $A^{10}$ are alkylene-O—;

$R^3$, $R^5$, $R^6$, and $R^8$ are hydrogen; and $R^1$, $R^2$, $R^4$, $R^7$, $R^9$, and $R^{10}$ are independently hydrogen, hydroxy, alkyl, alkylamine, alkenyl, substituted or unsubstituted aryl, arylalkyl, arylalkenyl, alkylphenyl, alkenylphenyl, alkylacyl, alkenylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

5. The compound according to claim 4, wherein $R^1$, $R^2$, $R^4$, $R^7$, $R^9$, and $R^{10}$ are independently alkyl, alkylamine, substituted or unsubstituted aryl, alkylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

6. The compound according to claim 5, wherein n is 1;

$R^1$ and $R^7$ are arylacyl; and $R^2$, $R^4$, $R^9$, and $R^{10}$ are amino acids.

7. The compound according to claim 6, wherein $R^2$, $R^4$, $R^9$, and $R^{10}$ are glycine, phenylalanine, tryptophan, or lysine.

8. The compound according to claim 1, wherein the compound has activity as an anti-endotoxin.

9. The compound according to claim 1, wherein the compound binds endotoxin.

10. The compound according to claim 1, wherein the compound binds lipid A.

11. The compound according to claim 1, wherein the compound has activity as a bactericidal agent.

12. A pharmaceutical composition comprising:

an oligocycloalkanoid compound according to claim 1 in a pharmaceutically acceptable carrier.

13. The pharmaceutical composition according to claim 12, wherein m and o are 1;

$A^3$, $A^5$, $A^6$, and $A^8$ are direct links and $A^1$, $A^2$, $A^4$, $A^7$, $A^9$, and $A^{10}$ are carbonyl; and $R^3$, $R^5$, $R^6$, and $R^8$ are hydrogen.

14. The pharmaceutical composition according to claim 13, wherein $R^1$, $R^2$, $R^4$, $R^7$, $R^9$, and $R^{10}$ are independently hydroxy, alkyl, aryl, aryloxy, amino, alkylamino, or arylalkylamino.

15. The pharmaceutical composition according to claim 12, wherein m and o are 1;

$A^3$, $A^5$, $A^6$, and $A^8$ are direct links and $A^1$, $A^2$, $A^4$, $A^7$, $A^9$, and $A^{10}$ are alkylene-O—;

$R^3$, $R^5$, $R^6$, and $R^8$ are hydrogen; and $R^1$, $R^2$, $R^4$, $R^7$, $R^9$, and $R^{10}$ are independently hydrogen, hydroxy, alkyl, alkylamine, alkenyl, substituted or unsubstituted aryl, arylalkyl, arylalkenyl, alkylphenyl, alkenylphenyl, alkylacyl, alkenylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

16. The pharmaceutical composition according to claim 15, wherein $R^1$, $R^2$, $R^4$, $R^7$, $R^9$, and $R^{10}$ are independently alkyl, alkylamine, substituted or unsubstituted aryl, alkylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

17. The pharmaceutical composition according to claim 15, wherein n is 1;

$R^1$ and $R^7$ are arylacyl; and $R^2$, $R^4$, $R^9$, and $R^{10}$ are amino acids.

18. The pharmaceutical composition according to claim 17, wherein $R^2$, $R^4$, $R^9$, and $R^{10}$ are independently glycine, phenylalanine, tryptophan, or lysine.

19. A method of treating a bacterial infection comprising:
providing an oligocycloalkanoid compound according to formula (I)

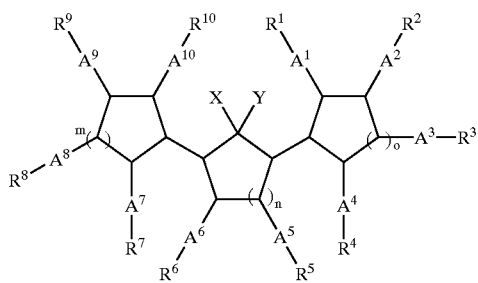

where m, n, and o are independently an integer from 0 to 2;
$A^1$ through $A^{10}$ are independently a direct link, alkylene, alkylene-O—, carbonyl, oxygen, or sulfur;
X and Y are independently hydrogen, hydroxy, alkyl, or in combination an electrophilic group; and
$R^1$ through $R^{10}$ are independently hydrogen, hydroxy, alkyl, alkenyl, alkynyl, substituted or unsubstituted aryl, N-, S-, or O-heterocycles, fused or multi-ring aryl with or without hetero ring members arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoalkylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, or polypeptide, with at least one of $R^1$ through $R^4$ and at least one of $R^7$ through $R^{10}$ being other than hydrogen; and
administering a bacteriacidally effective amount of the oligocycloalkanoid compound to a patient having a bacterial infection, under conditions effective to treat the bacterial infection.

20. The method according to claim 19, wherein said administering is carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes.

21. The method according to claim 19, wherein
m and o are 1;
$A^3$, $A^5$, $A^6$, and $A^8$ are direct links and $A^1$, $A^2$, $A^4$, $A^7$, $A^9$, and $A^{10}$ are alkylene-O—;
$R^3$, $R^5$, $R^6$, and $R^8$ are hydrogen; and
$R^1$, $R^2$, $R^4$, $R^7$, $R^9$, and $R^{10}$ are independently hydrogen, hydroxy, alkyl, alkylamine, alkenyl, substituted or unsubstituted aryl, arylalkyl, arylalkenyl, alkylphenyl, alkenylphenyl, alkylacyl, alkenylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

22. The method according to claim 21, wherein
$R^1$, $R^2$, $R^4$, $R^7$, $R^9$, and $R^{10}$ are independently alkyl, alkylamine, substituted or unsubstituted aryl, alkylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

23. The method according to claim 22, wherein
n is 1;
$R^1$ and $R^7$ are arylacyl; and
$R^2$, $R^4$, $R^9$, and $R^{10}$ are amino acids.

24. The method according to claim 23, wherein $R^2$, $R^4$, $R^9$, and $R^{10}$ are independently glycine, phenylalanine, tryptophan, or lysine.

25. A method of inhibiting or treating septic shock comprising:
providing an oligocycloalkanoid compound according to formula (I)

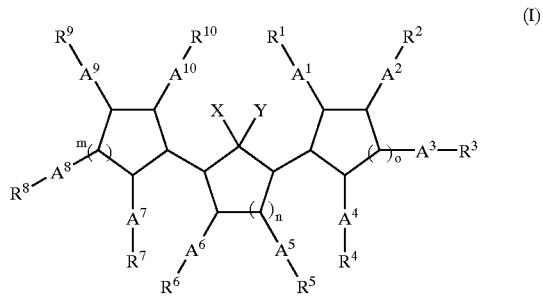

wherein m, n, and o are independently an integer from 0 to 2;
$A^1$ through $A^{10}$ are independently a direct link, alkylene, alkylene-O—, carbonyl, oxygen, or sulfur;
X and Y are independently hydrogen, hydroxy, alkyl, or in combination an electrophilic group; and
$R^1$ through $R^{10}$ are independently hydrogen, hydroxy, alkyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoalkylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, or polypeptide, with at least one of $R^1$ through $R^4$ and at least one of $R^7$ through $R^{10}$ being other than hydrogen; and
administering an effective amount of the oligocycloalkanoid compound to a patient having a bacterial infection, under conditions effective to inhibit or treat septic shock resulting from the bacterial infection.

26. The method according to claim 25, wherein said administering is carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes.

27. The method according to claim 25, wherein
m and o are 1;

$A^3$, $A^5$, $A^6$, and $A^8$ are direct links and $A^1$, $A^2$, $A^4$, $A^7$, $A^9$, and $A^{10}$ are alkylene-O—;

$R^3$, $R^5$, $R^6$, and $R^8$ are hydrogen; and $R^1$, $R^2$, $R^4$, $R^7$, $R^9$, and $R^{10}$ are independently hydrogen, hydroxy, alkyl, alkylamine, alkenyl, substituted or unsubstituted aryl, arylalkyl, arylalkenyl, alkylphenyl, alkenylphenyl, alkylacyl, alkenylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

28. The method according to claim 27, wherein
$R^1$, $R^2$, $R^4$, $R^7$, $R^9$, and $R^{10}$ are independently alkyl, alkylamine, substituted or unsubstituted aryl, alkylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

29. The method according to claim 28, wherein
n is 1;
$R^1$ and $R^7$ are arylacyl; and
$R^2$, $R^4$, $R^9$, and $R^{10}$ are amino acids.

30. The method according to claim 29, wherein $R^2$, $R^4$, $R^9$, and $R^{10}$ are independently glycine, phenylalanine, tryptophan, or lysine.

31. A method of treating a disease caused by bacterial endotoxin, said method comprising:
providing an oligocycloalkanoid compound according to formula (I)

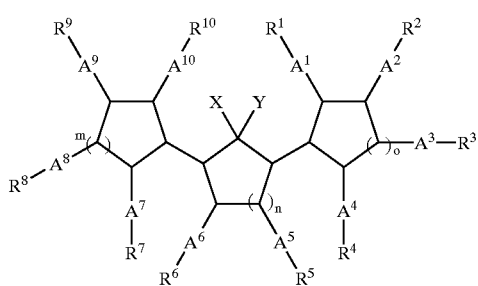

(I)

wherein m, n, and o are independently an integer from 0 to 2;

$A^1$ through $A^{10}$ are independently a direct link, alkylene, alkylene-O—, carbonyl, oxygen, or sulfur;

X and Y are independently hydrogen, hydroxy, alkyl, or in combination an electrophilic group; and $R^1$ through $R^{10}$ are independently hydrogen, hydroxy, alkyl, alkenyl, alkynyl, substituted or unsubstituted aryl, N-, S-, or O-heterocycles, fused or multi-ring aryl with or without hetero ring members, arylalkyl, arylalkenyl, arylalkyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoalkylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, or polypeptide, with at least one of $R^1$ through $R^4$ and at least one of $R^7$ through $R^{10}$ being other than hydrogen; and administering an effective amount of the oligocycloalkanoid compound to a patient having a bacterial infection, under conditions effective to neutralize bacterial endotoxin and thereby treat the disease caused bacterial endotoxin.

32. The method according to claim 31, wherein said administering is carried out orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes.

33. The method according to claim 31, wherein
m and o are 1;
$A^3$, $A^5$, $A^6$, and $A^8$ are direct links and $A^1$, $A^2$, $A^4$, $A^7$, $A^9$, and $A^{10}$ are alkylene-O—;
$R^3$, $R^5$, $R^6$, and $R^8$ are hydrogen; and
$R^1$, $R^2$, $R^4$, $R^7$, $R^9$, and $R^{10}$ are independently hydrogen, hydroxy, alkyl, alkylamine, alkenyl, substituted or unsubstituted aryl, arylalkyl, arylalkenyl, alkylphenyl, alkenylphenyl, alkylacyl, alkenylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

34. The method according to claim 33, wherein
$R^1$, $R^2$, $R^4$, $R^7$, $R^9$, and $R^{10}$ are independently alkyl, alkylamine, substituted or unsubstituted aryl, alkylacyl, arylacyl, aroyl, alkylaroyl, aminoaroyl, aminoalkylacyl, amino, alkylamino, alkenylamino, arylamino, dialkylamino, dialkenylamino, arylalkylamino, arylalkenylamino, amino acid, or polypeptide.

35. The method according to claim 34, wherein
n is 1;
$R^1$ and $R^7$ are arylacyl; and
$R^2$, $R^4$, $R^9$, and $R^{10}$ are amino acids.

36. The method according to claim 35, wherein $R^2$, $R^4$, $R^9$, and $R^{10}$ are independently glycine, phenylalanine, tryptophan, or lysine.

37. A method of inhibiting the activity of cathepsin K comprising:
providing an oligocycloalkanoid compound according to formula (I)

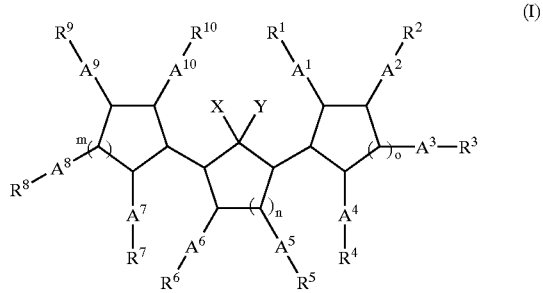

(I)

wherein m, n, and o are independently an integer from 0 to 2;

$A^1$ through $A^{10}$ are independently a direct link, alkylene, alkylene-O—, carbonyl, oxygen, or sulfur;

X and Y are independently hydrogen, hydroxy, alkyl, or in combination an electrophilic group; and $R^1$ through $R^{10}$ are independently hydrogen, hydroxy, allyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl alkynylacyl, arylacyl, aroyl, alkylaroyl, aminoaroyl, aminoalkylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, or polypeptide, with at least one of $R^1$ through $R^4$ and at least one of $R^7$ though $R^{10}$ being other than hydrogen; and introducing the oligocycloalkanoid compound into a system comprising cathepsin K under conditions effective to inhibit cathepsin K.

38. The method of claim 37, wherein the system is an in vitro system.

39. The method of claim 38, wherein the system is an in vivo system.

40. A method of making an oligocycloalkanoid compound comprising:

reacting a compound selected from the group of an $R^1$ to $R^{10}$ precursor, an oxidizing agent, a reducing agent, or a deprotecting agent with a compound according to formula (II) under conditions effective to prepare an oligocycloalkanoid compound according to claim 1

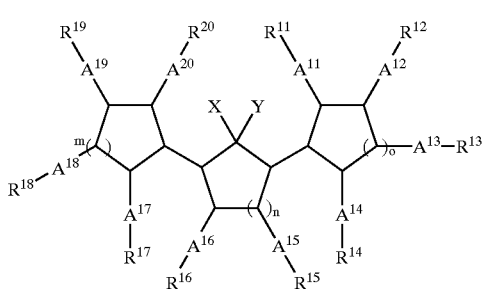

(II)

wherein m, n, and o are independently an integer from 0 to 2;

$A^{11}$–$A^{20}$ are independently alkylene, alkylene-O—, carbonyl, oxygen, or sulfur;

X and Y are independently hydrogen, hydroxy, alkyl, or in combination an electrophilic group; and $R^{11}$–$R^{20}$ are independently hydrogen, hydroxy, alkyl, alkenyl, alkynyl, substituted or unsubstituted aryl, N-, S-, or O-heterocycles, fused or multi-ring aryl with or without hetero ring members, arylalkyl, arylalkenyl, arylalkynyl, alkylphenyl, alkenylphenyl, alkynylphenyl, alkoxy, alkenyloxy, alkynyloxy, substituted or unsubstituted aryloxy, substituted or unsubstituted arylalkoxy, alkylacyl, alkenylacyl, alkynylacyl, arylacyl, aroyl, alkylaroyl, aminoaroyl, aminoalkylacyl, aminoalkyl, aminoalkenyl, aminoalkynyl, amino, alkylamino, alkenylamino, alkynylamino, arylamino, dialkylamino, dialkenylamino, dialkynylamino, arylalkylamino, arylalkenylamino, imino, alkylimino, alkenylimino, alkynylimino, arylimino, thiol, sulfoxide, alkyl sulfonamide, alkenyl sulfonamide, alkynyl sulfonamide, aryl sulfonamide, alkyl sulfonate ester, alkenyl sulfonate ester, alkynyl sulfonate ester, aryl sulfonate ester, amino acid, polypeptide, leaving group, or protecting group, with at least one of $R^{11}$ through $R^{14}$ and at least one of $R^{17}$ through $R^{20}$ being other than hydrogen.

41. The method according to claim 40, wherein at least one of $R^{11}$ to $R^{20}$ being a protecting group and the compound is a deprotecting agent.

42. The method according to claim 40, wherein the protecting group is a t-butyl carbamate protecting group, a 9-fluorenylmethyl carbamate protecting group, a trialkylsilyl-protected hydroxyether, or a trialkylsilyl-protected hydroxy ester.

43. The method according to claim 42, wherein the deprotecting agent is either trifluoroacetic acid in methylene chloride, piperidine in dimethylformamide, or tetra-n-butylammonium fluoride in tetrahydrofuran.

44. The method according to claim 40, wherein the compound is an oxidizing agent.

45. The method according to claim 40, wherein the compound is a reducing agent.

46. The method according to claim 40, wherein the compound is an $R^1$ to $R^{10}$ precursor.

47. An oligocycloalkanoid compound comprising formula (I)

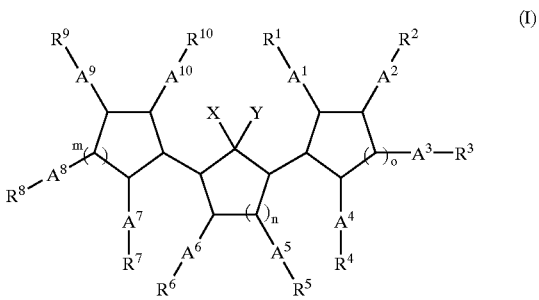

(I)

wherein m and o are 1 and n is an integer from 0 to 2;

$A^1$, $A^2$, $A^4$, $A^7$, $A^9$, and $A^{10}$ are carbonyl and $A^3$, $A^5$, $A^6$, and $A^8$ are direct links;

X and Y are hydrogen or X and Y in combination are a keto group;

$R^3$, $R^5$, $R^6$, $R^8$ are hydrogen;

$R^1$ and $R^{10}$ are independently straight-chain or branched-chain alkyl or alkoxy; and $R^2$, $R^4$, $R^7$, and $R^9$ are independently hydroxy, straight-chain or branched-chain alkyl, straight-chain or branched-chain alkoxy, alkylamino, phenylethoxy, 3-phenylpropoxy, or phenylalkylamino.

48. The compound according to claim 47 wherein n is 1, $R^1$ and $R^{10}$ are tert-butyl groups, $R^2$ and $R^9$ are alkylamino groups, and $R^4$ and $R^7$ are phenylalkylamino groups.

49. A pharmaceutical composition comprising:

an oligocycloalkanoid compound according to claim 47 in a pharmaceutically acceptable carrier.

50. A method of treating a bacterial infection comprising:

providing an oligocycloalkanoid compound according to claim 47 and administering a bacteriacidally effective amount of the oligocycloalkanoid compound to a patient having a bacterial infection, under conditions effective to treat the bacterial infection.

51. A method of treating a disease caused by bacterial endotoxin, said method comprising:

providing an oligocycloalkanoid compound according to claim 47 and administering an effective amount of the oligocycloalkanoid compound to a patient having a bacterial infection, under conditions effective to neutralize bacterial endotoxin and thereby treat the disease caused bacterial endotoxin.

52. A method of inhibiting the activity of cathepsin K comprising:

providing an oligocycloalkanoid compound according to claim 47 and introducing the oligocycloalkanoid compound into a system comprising cathepsin K under conditions effective to inhibit cathepsin K.

* * * * *